US008894637B2

(12) United States Patent
Ben-Yakar et al.

(10) Patent No.: US 8,894,637 B2
(45) Date of Patent: Nov. 25, 2014

(54) SYSTEMS, DEVICES AND METHODS FOR IMAGING AND SURGERY

(75) Inventors: Adela Ben-Yakar, Austin, TX (US); Christopher L. Hoy, Austin, TX (US); Olav Solgaard, Stanford, CA (US)

(73) Assignees: Board of Regents, The University of Texas System, Austin, TX (US); The Board of Trustees of the Leland Stanford Junior University, Palo Alto, CA (US)

(*) Notice: Subject to any disclaimer, the term of this patent is extended or adjusted under 35 U.S.C. 154(b) by 125 days.

(21) Appl. No.: 12/811,888

(22) PCT Filed: Jan. 22, 2009

(86) PCT No.: PCT/US2009/031694
§ 371 (c)(1),
(2), (4) Date: Jul. 7, 2010

(87) PCT Pub. No.: WO2009/094451
PCT Pub. Date: Jul. 30, 2009

(65) Prior Publication Data
US 2010/0286674 A1    Nov. 11, 2010

Related U.S. Application Data

(60) Provisional application No. 61/022,544, filed on Jan. 22, 2008.

(51) Int. Cl.
A61B 18/18     (2006.01)
A61B 5/00      (2006.01)
G01N 21/64     (2006.01)
G01N 21/47     (2006.01)
G01B 9/04      (2006.01)
A61B 18/20     (2006.01)
A61B 19/00     (2006.01)

(52) U.S. Cl.
CPC .............. *G01B 9/04* (2013.01); *A61B 5/0059* (2013.01); *G01N 21/6458* (2013.01); *G01N 21/4795* (2013.01); *A61B 5/6852* (2013.01); *A61B 2018/2085* (2013.01); *A61B 19/5223* (2013.01); *A61B 5/0066* (2013.01); *A61B 18/20* (2013.01)
USPC ......................................................... 606/16

(58) Field of Classification Search
USPC ............ 977/810, 890, 915; 428/364; 606/16; 372/6; 607/89; 250/492.1
See application file for complete search history.

(56) References Cited

U.S. PATENT DOCUMENTS 5,112,328 A    5/1992    Taboada et al.
5,178,616 A    1/1993    Uemiya et al.

(Continued)

FOREIGN PATENT DOCUMENTS

GB    2338568    12/1999
GB    2341943    3/2000

(Continued)

OTHER PUBLICATIONS

Flusberg, BA et al. "Fiber-optic fluorescence imaging," Nat Methods. 2(12): 941-950, (Dec. 2005).*

(Continued)

*Primary Examiner* — Colleen A Matthews
*Assistant Examiner* — Tuan Nguyen
(74) *Attorney, Agent, or Firm* — Meunier Carlin & Curfman, LLC

(57) ABSTRACT

Provided herein are devices, systems and methods for imaging of biological tissue. Also provided are devices, systems and methods for surgical manipulation of biological tissue. Further provided are devices, systems and methods for combined imaging and surgical manipulation of biological tissue.

65 Claims, 10 Drawing Sheets

(56) References Cited

U.S. PATENT DOCUMENTS

| | | | |
|---|---|---|---|
| 5,720,894 | A | 2/1998 | Neev et al. |
| 5,785,704 | A | 7/1998 | Bille et al. |
| 5,893,830 | A | 4/1999 | Zeitels |
| 5,995,867 | A | 11/1999 | Zavislan et al. |
| 6,451,009 | B1 | 9/2002 | Dasilva et al. |
| 6,620,180 | B1 | 9/2003 | Bays et al. |
| 6,778,902 | B2 | 8/2004 | Hathiram et al. |
| 6,839,586 | B2 | 1/2005 | Webb |
| 6,975,898 | B2 | 12/2005 | Seibel |
| 7,050,906 | B2 | 5/2006 | Hathiram et al. |
| 7,131,968 | B2 | 11/2006 | Bendett et al. |
| 7,167,622 | B2 | 1/2007 | Temelkuran et al. |
| 7,172,588 | B2 | 2/2007 | Stingl et al. |
| 7,218,446 | B2 | 5/2007 | Dixon et al. |
| 2005/0107852 | A1 | 5/2005 | Levernier et al. |
| 2005/0154380 | A1 | 7/2005 | DeBenedictis et al. |
| 2006/0142746 | A1* | 6/2006 | Friedman et al. ............ 606/11 |
| 2006/0195076 | A1 | 8/2006 | Blumenkranz et al. |
| 2007/0213618 | A1 | 9/2007 | Li et al. |
| 2008/0058780 | A1* | 3/2008 | Vogler ........................... 606/5 |
| 2008/0269731 | A1* | 10/2008 | Swinger et al. ................ 606/5 |
| 2009/0099595 | A1 | 4/2009 | Cheng et al. |

FOREIGN PATENT DOCUMENTS

| | | |
|---|---|---|
| WO | 2009094451 A2 | 7/2009 |
| WO | 2011091283 A1 | 7/2011 |

OTHER PUBLICATIONS

Fluesberg, BA et al. "Fiber-optic fluorescence imaging," Nat Methods. 2(12): 941-950, (Dec. 2005).*

Bird, D. et al. "Two-photon fluorescence endoscopy with a micro-optic scanning head," Opt. Lett., 28(17):1552-4, (Sep. 1, 2003).

Flusberg, BA et al. "Fiber-optic fluorescence imaging," Nat Methods. 2(12):941-950, (Dec. 2005).

Flusberg, BA et al. "In vivo brain imaging using a portable 3.9 gram two-photon fluorescence microendoscope," Opt. Lett. 30(17):2272-4, (Sep. 1, 2005).

Girard, B et al. "Microtomographic Analysis of Healing of Femtosecond Laser Bone Calvarial Wounds Compared to Mechanical Instruments in Mice With and Without Application of BMP-7," Lasers in Surgery and Medicine 39:458-467 (2007).

Gobel, W. et al. "Miniaturized two-photon microscope based on a flexible coherent fiber bundle and a gradient-index lens objective," Opt Lett., 29(21):2521-3, (Sep. 1, 2005).

Goetz, MH et al. "Computer-guided laser probe for ablation of brain tumours with ultrashort laser pulses," Phys. Med. Biol. 44 N119-N127, (1999).

Helmchen F. et al. "A miniature head-mounted two-photon microscope. high-resolution brain imaging in freely moving animals," Neuron, 31(6):903-12, (Sep. 27, 2001).

Horn, M. et al. "The use of confocal laser-scanning microscopy in microsurgery for invasive squamous cell carcinoma," J. Derm. 156, 81-84. (2007).

Hoy, C.L. et al. "A Compact Scanning Head for Simultaneous Two-Photon Imaging and fs-Laser Microsurgery," Presentation. SPIE Photonics West 2007. The Ben-Yakar Group—The University of Texas at Austin. (Jan. 22, 2007).

Hoy, Christopher et al. "Miniaturized probe for femtosecond laser microsurgery and two-photon imaging," Optics Express 9996, 16(13), (Jun. 23, 2008).

Hoy, Christopher et al. "A Miniature Microscope for Two-Photon Imaging and Femtosecond Laser Surgery," Conference Paper, Frontiers in Optics (FiO) San Jose, California, (Sep. 16, 2007).

Kim, D. et al. "High-speed handheld multiphoton multifoci microscopy," Multiphoton microscopy in the biomedical sciences IV, at Biomedical Optics 2001 San Jose, CA, SPIE Proc., 5323, 267-272, (2004).

Lee, D. and Solgaard, O. "Two-axis gimbaled microscanner in double SOI layers actuated by self-aligned vertical electrostatic combdrive." in proceedings of Solid-State Sensors, Actuators and Microsystems Workshop, Hilton Head Island, 352-355, (2004).

Leppert, J. et al. "Multiphoton excitation of autofluorescence for microscopy of glioma tissue," Neurosurgery vol. 58, Issue 4, 759-767, (2006).

Loesel, FH et al. "Non-thermal ablation of neural tissue with femtosecond laser pulses," Appl. Phys. B 66, 121-128, (1998).

Skala M.C. et al. "Multiphoton microscopy of endogenous fluorescence differentiates normal, precancerous, and cancerous squamous epithelial tissues," Cancer Research 65, 180-186, (2005).

Thomas, T.P. et al. "Detection and analysis of tumor fluorescence using a two-photon optical fiber probe," Biophys. J. 86, 3959-3965, (Jun. 2004).

Vogel, A. et al. "Mechanisms of femtosecond laser nanosurgery of cells and tissues," Applied Physics B: Lasers and Optics. 81(8):1015-1047, (2005).

Wilder-Smith et al. "In Vivo Multiphoton Fluorescence Imaging: A Novel Approach to Oral Malignancy," Lasers in Surgery and Med. 35, 196-103, (2004).

Yanik et al. "Functional regeneration after laser axotomy," Nature 432, 822, (2004).

International Search Report, dated Aug. 21, 2009, in corresponding International Application No. PCT/US2009/031694.

International Search Report, dated Mar. 28, 2011, in related International Application No. PCT/US2011/022099.

International Preliminary Report on Patentability and Written Opinion, dated Jul. 24, 2012, in related International Application No. PCT/US2011/022099.

Copending U.S. Appl. No. 13/574,472, filed Jan. 14, 2013.

Wahrburg, J., et al., "Concept of a Novel Laser Probe for Minimal Invasive Applications in Neurosurgery," Mechatronics in Surgery, vol. 6, issue 4, 1996, pp. 479-489.

Wisweh, Henning, et al., "Optical coherence tomography monitoring of vocal fold femtosecond laser microsurgery," Proceedings of the European Conferences on Biomedical Optics, 2007, 7 pages. Retrieved from http://www.dmphotonics.com/Optical-Coherence_Tomography/Optical%20coherence%20tomography%20monitoring.pdf.

* cited by examiner

US 8,894,637 B2

SYSTEMS, DEVICES AND METHODS FOR IMAGING AND SURGERY

CROSS REFERENCE TO RELATED APPLICATIONS

This application claims the benefit of U.S. Provisional Application No. 61/022,544, filed Jan. 22, 2008, which is incorporated by reference in its entirety as part of this application.

STATEMENT REGARDING FEDERALLY SPONSORED RESEARCH

This invention was made with government support under Grant No. BES-0548673 awarded by the National Science Foundation. The government has certain rights in the invention.

BACKGROUND

Precision imaging and surgical manipulation of biological tissue can be used to improve medical treatment outcomes.

SUMMARY

Provided herein are devices, systems and methods for imaging and/or for surgical manipulation of biological tissue. An example system for surgical manipulation of biological tissue in a subject comprises an ultra-fast pulsed surgical laser light source configured to produce laser light for surgical manipulation of biological tissue, an optical delivery fiber and an objective lens. The optical delivery fiber can be configured to direct light from the surgical laser light source for transmission to the objective lens and the objective lens can be configured to transmit light to a region of interest in the subject for surgical manipulation of biological tissue.

The example system can further comprise an imaging light source configured to produce light for imaging of biological tissue and a pair of relay lenses. Light from the imaging light source can be configured to be directed through the pair of relay lenses for transmission to the objective lens and the objective lens can be configured to transmit light from the imaging light source to a region of interest in the subject and to receive light from the region of interest in the subject for imaging of biological tissue.

An example system for imaging biological tissue in a subject comprises an imaging light source configured to produce light for imaging of biological tissue, an optical delivery fiber, a pair of relay lenses, and an objective lens. The optical delivery fiber can be configured to direct light from the imaging light source through the pair of relay lenses for transmission onto the objective lens, and the objective lens can be configured to direct light transmitted onto it from the imaging light source to a region of interest in the subject. The objective lens is also configured to receive light from the region of interest. The system can further comprise a photodetector configured to detect at least a portion of the light received from the region of interest. Moreover, the system can also comprise an ultra-fast pulsed surgical laser light source configured to produce laser light for surgical manipulation of biological tissue. Produced laser light can be configured to be directed from the ultra-fast pulsed surgical laser light source to the objective lens and the objective lens can be configured to transmit light from the ultra-fast surgical laser light source to a region of interest in the subject for surgical manipulation of biological tissue.

An example device for surgical manipulation of biological tissue in a subject comprises an optical delivery fiber and an objective lens. The optical delivery fiber can be configured to direct light from an ultra-fast pulsed surgical laser light source for transmission to the objective lens and the objective lens can be configured to transmit light from the ultra-fast pulsed surgical laser light source directed to it to a region of interest in the subject for surgical manipulation of biological tissue in the subject. The device can further comprise a pair of relay lenses. Light from an imaging light source can be configured to be directed through the pair of relay lenses for transmission to the objective lens and the objective lens can be configured to transmit light from the imaging light source directed to it to a region of interest in the subject and to receive light from the region of interest in the subject for imaging of biological tissue in the subject.

An example device for imaging biological tissue in a subject comprises an optical delivery fiber, a pair of relay lenses and an objective lens. The optical delivery fiber can be configured to direct light from an imaging light source through the pair of relay lenses for transmission onto the objective lens and the objective lens can be configured to direct light transmitted onto it from the imaging light source to a region of interest in the subject. The objective lens is also configured to receive light from the region of interest for imaging biological tissue. The optical delivery fiber can be further configured to direct light from an ultra-fast pulsed surgical laser light source to the objective lens and the objective lens can be configured to transmit light from the surgical laser light source to a region of interest in the subject for surgical manipulation of biological tissue in the subject.

DETAILED DESCRIPTION

Provided herein are devices, systems and methods for imaging and/or for surgical manipulation of biological tissue. Biological tissue can be located in a subject. For example, the biological tissue can be located in, or can be derived from, a human or non-human animal. Biological tissue can comprise any tissue, or portion thereof, of, or derived from an organism, such as a mammal. Biological tissue can comprise a cell, a collection of cells, or portions of a cell or cells. Biological tissue also includes organized tissues such as, for example, organs or portions thereof. Biological tissue can be normal or diseased. For example, biological tissue can comprise a cancerous or precancerous cell or collections of cancerous or precancerous cells.

Figure 1:
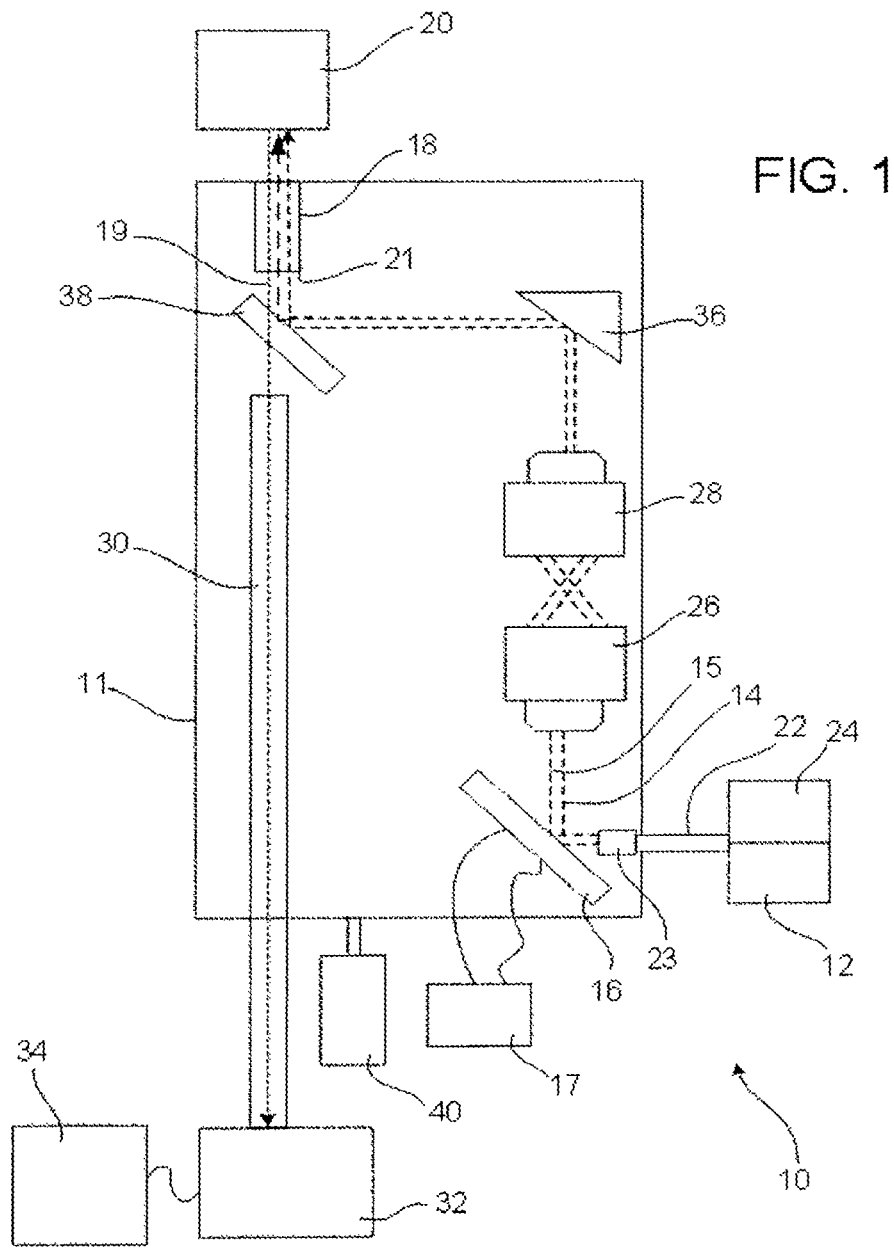
FIG. 1 is a schematic diagram illustrating an example multiphoton imaging and surgical system.

FIG. 1 is a schematic diagram illustrating an example system 10 for surgical manipulation of biological tissue and/or for multi-photon imaging. The imaging and surgical manipulation can be performed in a subject. The system comprises an ultrafast pulsed laser surgical light source 12. The terms ultrafast and ultrashort are used interchangeably herein. The light source 12 is configured to produce laser light for surgical manipulation of biological tissue in the subject. For example, the light source 12 can be configured to produce one or more pulses of laser light having a duration of less than one nanosecond. Optionally, the light source 12 is a picosecond or a femtosecond laser light source comprising a laser that can generate one or more laser pulses having durations in the picosecond or femtosecond time regime. The light source 12 can also be configured to produce laser pulses that are near-infrared.

Femtosecond lasers can be used as an ultrashort laser pulse source for multiphoton imaging and femtosecond laser microsurgery techniques described herein. Femtosecond lasers are any laser which emits laser pulses with pulse duration between and including 1 ps and 1 fs. The femtosecond lasers can be solid state lasers which utilize a broadband gain medium, such as titanium-doped sapphire or chromium-doped forsterite crystals. In such lasers, femtosecond laser pulses can be created when mode-locking is achieved, either passively or actively, and the constructive interference between intracavity modes results in a powerful ultrashort pulse of laser light. A picosecond laser can produce pulses between and including 1 ns and 1 ps.

Femtosecond laser pulses of higher intensity can be created using an optical amplifier, most commonly a chirped-pulse amplifier or an optical parametric amplifier. In both an oscillator and amplifier systems, femtosecond laser pulses are most commonly in the near-infrared wavelength range, approximately 600 nm to 1000 nm, where biological tissue is largely transparent.

As used herein, surgical manipulation includes photodamage of biological tissue located in a subject. Thus, in vivo or ex vivo biological tissue can be targeted for surgical manipulation using the described systems. The photodamage can be located in a focal volume where light from the light source 12 is focused. The focal volume can be located in a target tissue. Application of light from the light source 12 using the described systems can cause ablation of tissue in the subject. Such ablation can also be confined to a focal volume located in the tissue.

The ultra-fast surgical laser light source 12 is located in communication with an optical delivery fiber 22. The optical delivery fiber transmits surgical light 14 from the light source 12 into a housing 11. An objective lens 18 is also located in conjunction with the housing 11. The objective lens 18 is configured to receive light generated by the light source 12 that is transmitted into the housing 11 by the optical delivery fiber 22. The objective lens 18 can optionally be a gradient index (GRIN) lens, an aspheric lens, a spherical lens, a chromatic doublet, and the like. Z-scanning can be used, which is the scanning of focused laser light towards or away from the target tissue. This can be accomplished by moving the system 10 or portions thereof towards or away from the target tissue. For example, the objective lens 18 can be actuated to move towards or away from the target tissue using a MEMS actuator or a PZT actuator. Similarly the housing, including the objective lens 18 can be actuated to move towards or away from the target tissue using a MEMS actuator or a PZT actuator. The objective lens 18 can be moved, for example, by MEMS devices or piezoelectric devices.

Optionally, the optical delivery fiber 22 is an air-core photonic crystal fiber (PCF). Light transmitted along the fiber 22 can be directed through a collimating lens 23 and onto a scanning device 16. In other examples, instead of a scanning device 16, the optical delivery fiber 22 can be moved to provide scanning of light from the light source 12. For example, the fiber 22 can be moved using a piezoelectric scanning device that is configured to move the fiber to scan light from the light source 12.

The scanning device 16 can optionally be a microelectromechanical (MEMS) scanner. Example scanning devices 16 also include an electro-optic crystal, a rotating wedge prism, and piezoelectric devices. If a MEMS scanner is used, it can be a two-axis gimbaled scanner with a reflective surface. The reflective surface can comprise a reflective coating that comprises metal. For example, the metal coating can comprise silver or aluminum. The scanning device 16 can be actuated to scan light from the optical delivery fiber 22 for transmission to the objective lens 18. For example, at least one processing unit 17 can be in communication with the scanning device 16. The processing unit 17 can be used to control the actuated movement of the scanning device 16 for direction of light from the optical delivery fiber 22 to the objective lens 18. The scanning device 16 is also located in the housing 11 and the housing can be sized for endoscopic in vivo surgical procedures in the subject. Portions of the system 10 can be referred to as a probe. For example, when the housing 11, or other portions of the system are configured for surgical manipulation and/or imaging in a human or non-human subject, portions of the system can be referred to as a probe.

Light from the ultra-fast pulsed surgical laser light source 12, surgical light 14, directed onto the scanning device 16 can be further directed through a pair of relay lenses 26 and 28 prior to contacting the back aperture 21 of the objective lens 18. Each relay lens of the pair 26 and 28 can be an aspherical lens. Optionally, the numerical aperture of each relay lens is 0.9 or less. Also, optionally, the surgical light 14 from the light source 12 can contact a mirror 36 subsequent to passing through the relay lens 28. The surgical light 14 from the light source 12 can also be directed to the objective lens 18 using a hot mirror 38. At least a portion of the surgical light 14 from the light source 12 that contacts the back aperture 21 of the objective lens 18 is transmitted onto a region of interest or target tissue 20 of the subject. Thus, target tissue can be a region if interest in a subject.

The objective lens 18 can focus surgical light 14 from the light source 12 into a focal volume where surgical manipulation can occur by the focused surgical light 14. The objective lens 18 can have a numerical aperture of 0.4 or higher. As described above, the surgical light 14 can cause photodamage or ablation of tissue in the subject. An actuator device 40, such as an electric motor, can be used to move the housing 11 towards or away from the target tissue 20. In some aspects, the system 10, or portions thereof, such as the housing 11, can be moved in a ferrule using a piezoelectric device or micromotor.

The system 10 can further comprise a light source 24 for multi-photon imaging. The imaging light source 24 can be a pulsed laser light source used for multi-photon imaging. Although the light source for surgery 12 and the light source for imaging 24 are separately depicted in this example, in other examples, the same light source can be used for both surgery and imaging. In these other examples, the light source can be adjustable such that it can produce surgical light 14 and imaging light 15. Optionally, the light having the same characteristics can be used for imaging and surgery. Thus, a system comprising an ultra-fast pulsed surgical laser light source and further comprising an imaging light source can include one light emitting component that can produce light configured for imaging and light configured for surgery. In some examples, the light for imaging and for surgery will have the same or similar characteristics such as, for example, wavelength and pulse duration.

The imaging light source 24 can therefore be configured to produce light for imaging of biological tissue, referred to herein as imaging light 15. Similar to the surgical light 14, the imaging light 15 can be transmitted along the optical delivery fiber 22, through the collimating lens 23 and onto a scanning device 16. The imaging light 15 can be further directed through the pair of relay lenses 26 and 28 and through the objective lens 18. Before being transmitted through the objective lens 18, the imaging light 15 can contact the mirror 36 and mirror 38, which guide the imaging light 15 on to the back aperture 21 of the objective lens 18. The objective lens 18 is configured to transmit imaging light 15 to a region of interest or target tissue 20.

The objective lens 18 is further configured to receive light 19 from the target tissue 20. Light received 19 from the target tissue 20 can comprise light resulting from excitation of fluorophores in the target tissue. The excitation of the fluorophores can be caused by interaction of the imaging light 15 and the target tissue. Light received from the target tissue can also result from luminescence from nanoparticles located in the target tissue 20. For example, gold luminescence from nanoparticles can be received. Further, the light received from the target tissue can result from the generation of a second harmonic of light incident on a region of interest of the target tissue. The second harmonic can be produced from the interaction of the target tissue and the imaging light 15.

Thus, multiphoton imaging refers to methods of imaging or visualization which utilizes the fluorescent or luminescent emission light stemming from a multiphoton process event. For multiphoton imaging using the described system, a train of ultrashort laser pulses can optionally be focused into the sample or target tissue 20 to be imaged. At the focal volume, the light intensities are sufficiently high to induce nonlinear processes involving the simultaneous absorption of multiple photons. Examples of these processes are two- and three-photon absorption, second harmonic generation, and two-photon luminescence. The light emitted from the multiphoton process is collected and detected by the photodetector 32, such that an electrical signal is generated which is proportional to the amount of emitted photons collected. By scanning the focused laser beam collecting emitted light at successive positions in the target tissue, an image can be reconstructed by mapping the detected light signals to corresponding locations in an image.

In addition to imaging based on the intensity of the collected emission light (e.g received light 19), extra information about the sample can be gained by additional analysis of the collected light. In one method, the collected light can be sent to a spectrometer and spectral information can be assigned to each location in the reconstructed image. In another method, the collected light can be sent to a single-photon counting detector and can be used to assign fluorescent lifetime information to each location in the reconstructed image.

At least a portion of the light received by the objective lens 18 from the target tissue can be transmitted to an optical transmitter 30. In the system 10, the hot mirror 38 allows for passage of light from the objective lens 18 and into communication with the optical transmitter 30. The optical transmitter 30 can transmit light received from the target tissue to the photodetector 32. The photodetector 32 is configured to detect at least a portion of the light transmitted along the optical transmitter 30. The photodetector can be in communication with at least one processing device 34 which can produce an image from light detected by the photodetector 32.

Portions of the system 10 can be located in the housing 11. Some portions of the system can also be located outside of the housing 11. As described above, the housing 11 can be moved towards or away form the target tissue 20 using an actuating device. The system 10 can be used for surgical manipulation of biological tissue using light from the light source 12. Optionally, the system 10 can be used for multi-photon imaging in addition to its use for surgical manipulation of biological tissue. The system 10 can also be used for multi-photon imaging alone. Optionally, the system 10 can be used for surgical manipulation of biological tissue in addition to its use for multi-photon imaging.

Whether the system 10 is used for surgical manipulation of biological tissue alone, multi-photon imaging alone, or both surgical manipulation of biological tissue and multi-photon imaging can be determined by an operator of the system. For example, if only surgical manipulation of biological tissue is desired, the system 10 can be used to transmit surgical light 14 to the target tissue. If only multi-photon imaging is desired, the system 10 can be used to transmit imaging light 15 to the target tissue. If both multi-photon imaging and surgical manipulation of biological tissue is desired, the system can be used to transmit imaging light 15 and surgical light 14 to the target tissue.

Thus, provided herein are methods, systems, and devices for multiphoton microscopy and ultrashort pulsed laser surgery. In one aspect, provided is a miniaturized sized probe configured for multiphoton microscopy and ultrashort pulse laser surgery.

The system 10 can be used to enhance field of view (FOV), resolution, and collection efficiency without the trade-offs normally encountered in miniaturized multiphoton fluorescent microscope designs. This can be achieved with a miniature optical system between the scanning device 16 and the imaging objective lens 18. The example system 10 can be used for targeted delivery of higher-energy ultrashort pulses for combined ultrashort-pulse laser micro-/nanosurgery and multiphoton imaging. The result is a system 10 that can be used for combined medical diagnosis and treatment of diseased tissues and for investigation of various biological tissues. In one aspect, the system 10 can provide for real-time diagnosis and removal of small cancerous lesions in skin, in body cavities or intraoperatively.

The imaging system 10 can be used to image the scanning device 16 to the objective lens 18, such that the surgical 14 and/or imaging light 15 do not move along the plane of back aperture 21 of the objective lens 18 during scanning. This allows for the whole scanning angle of the scanning device 16 to be used without being limited by the distance to the objective lens 18 or the size of the objective lens 18. This way the FOV can be enlarged without degrading resolution.

The system 10 also provides a method of expansion of the surgical light 14 and or the imaging light 15, wherein either light beam size can be small at the scanner 16 so as to reduce diffraction and can be large at the objective 18 to increase resolution.

By imaging the scanner 16 to the objective lens 18, the scanning device 16 can be moved away from the objective lens 18 which allows collection optics, such as the optical transmitter 30, to be placed close to the objective 18 to enhance collection efficiency. By integrating higher-energy ultrashort pulses, ultrashort-pulse laser micro-/nanosurgery can be achieved which provides precision ablation of specifically targeted nanoscale structures, such as organelles or axons with less collateral damage when compared to conventional continuous wave and long pulse (>1 ns) lasers. In addition, the system 10 allows for scanning of the surgical light 14 for ablation of larger tissue regions.

In one aspect, provided are methods, systems, and devices for combined multiphoton microscopy and ultrashort pulse laser surgery of biological tissues through a selectively sized probe. The probe can comprise the housing 11. Laser surgery can comprise micro-surgery, nano-surgery, and the like. The system 10 can comprise a scanning device 16, which can be miniaturized, and can optionally scan a pulse train of near-infrared laser pulses lasting between 100 and 1/100th of a picosecond in duration about two axes, a pair relay lenses (26 and 28), which can optionally be miniaturized positive lenses that can be used to image the location of the scanning device to the back aperture of an objective lens 18. The objective lens 18 can optionally focus laser light into the sample (e.g. the target tissue 20).

For microscopy, laser light can excite intrinsic fluorophores (autofluorescence), exogenous fluorophores, and/or metallic nanoparticles. The light emitted from these (fluorescence or luminescence) can be collected through the objective lens 18. In addition to use of metallic nanoparticles for imaging of luminescence, those same nanoparticles can be used during the surgical uses of the disclosed apparatus by using the ultrashort pulse laser source to excite the plasmon resonance of the nanoparticles and ablating at the particles through the near-field enhancement effect.

Light received by the objective lens 18 (collected light from the sample 20) can pass through a dichroic mirror or hot mirror 38 and be collected by a optical transmitter 30, such as an optical fiber. The system 10 can be used in conjunction with higher-energy ultrashort laser pulses for microsurgery of biological tissues. Optionally, the only foci inside the system are located in air and the light propagation through glass or plastic is reduced by optionally eliminating long relay gradient index (GRIN) lenses of the type sometimes found in multiphoton endoscope designs. For micro/nanosurgery, the surgical light 14 focused into the target tissue 20 can be of sufficient intensity to cause intentional photodamage either through ablation or indirect bond breaking due to free electron formation.

As described above, the scanning device 16 can optionally be a MEMS scanner. The scanning device 16 can optionally comprise a MEMS mirror with a diameter slightly larger diameter of the light projected onto it. The relay lens pair 26 and 28 can optionally comprise miniature molded aspherical lenses, wherein the numerical apertures of each lens is less than 0.9. The relay lens pair (26 and 28) also provides a method of light beam expansion, wherein the beam size of the imaging light 15 and/or surgical light 14 can be small at the scanning device 16 so as to reduce diffraction and can be large at the objective lens 18 to increase resolution.

The system 10 can be optionally used for the combination of ultrashort-pulse laser micro-/nanosurgery and multiphoton microscopy in a miniaturized device. Ultrashort-pulse laser micro-/nanosurgery provides a high-precision tool for making subcellular incisions, ablating nanoscale structures, and modifying organelles and axons. The surgical manipulations of biological tissue such as incisions can be directed to a specific point of interest or scanned to modify a large collection of cells. The system 10 can be used to destroy diseased cells, such as small neoplastic lesions, in real-time during a diagnostic imaging process. For example, the system 10 can be used for the targeting of neoplastic lesions and precancerous cells, for which there are currently no imaging modalities capable of diagnosing small (<2 mm) lesions in the epithelium without a lengthy and invasive biopsy process.

The system 10, or portions thereof, such as the housing 11, can be used as surface probe device, able to access large body cavities (i.e. mouth) and can be used intraoperatively. The system 10, or portions thereof, such as the housing 11, can also be manufactured through nanolithography of silicon for a microscope-on-a-chip, which can fit into commercial endoscope housings for colorectal, tracheal, GI, and esophageal (and other) applications. The system 10, or portions thereof, such as the housing 11, can be coupled with a means of aspiration in an endoscopic probe so that a laser microsurgery technique can be used to excise tissue sections for analysis. For example, surgical light 14, such as laser, can be used to cut away the region of interest, which can be aspirated and analyzed in a flow cytometry assay for detection of various pathologies. The system 10, or portions thereof, such as the housing 11, can be adapted for a disposable endoscope system. The system 10, or portions thereof, such as the housing 11, can be sized to be positioned inside a body cavity, sized to be used endoscopically within the accessory channel of commercially available endoscope devices or as a stand-alone device, sized to be used as a handheld device, both externally and intraoperatively in surgically created body cavities and openings.

As described above, metallic nanoparticles for imaging of luminescence can be used, and metallic nanoparticles can also be used during the surgical operation of the system 10 by using an ultrashort pulsed laser source to excite the plasmon resonance of the nanoparticles and ablating at the particles through the near-field enhancement effect.

A focusing lens, such as an objective lens, can be used to focus surgical light 14 and imaging light 15, such as femtosecond laser pulses, into the core of the optical fiber 22. The optical fiber 22 can be hollow-core fiber, which can be created by utilizing a photonic bandgap to confine light in a defect region making up the core of the fiber. The focusing lens can be chosen such that the numerical aperture of the lens is less than that of the optical fiber 22 and that the resulting focused laser spot size is smaller than the core size of the optical fiber 22, which will result in efficient coupling of the free-space light into the optical fiber 22. If used, the hollow-core photonic crystal fiber then transmits the laser light by guiding it in a single transverse mode (TEM00) to the housing 11, where the collimating lens 23 collimates the transmitted laser light.

Pre-chirping of the surgical light 14 or imaging light 15, such as a femtosecond laser pulse, can be performed to compensate for dispersion in the optical fiber 22. Additionally, wavelengths can be chosen at or near the zero dispersion wavelength of the optical fiber 22 to reduce dispersion. Pre-chirping is a technique for causing chirping in light pulses that compensates for chirping caused in a transmitter. For example, two types of chirping that can be used include blue chirping that causes the wavelength to shift to the longer wavelength side at the rising of an output pulse and to the shorter wavelength side at the falling thereof, and red chirping that causes the wavelength to shift to the shorter wavelength side at the rising of an output pulse and to the longer wavelength side at the falling thereof, and the type of chirping is selected depending on the fiber mainly used in the transmission channel.

The system 10 can further comprise a beamsplitter such as the hot mirror 38 to separate excitation and emission light. A beamsplitter can separate light by wavelength and can be an element with a dichroic coating which is reflective to a certain wavelength range, such as that of the excitation laser light, and is transmissive to another wavelength range, such as that of the emitted fluorescent light.

Optionally, the system 10 can be used for femtosecond laser microsurgery, which is a technique for precise manipulation of biological tissues with reduced damage to surrounding tissues. The combination of this technique with two-photon imaging provides a non-invasive means of visualization to guide such surgery in situ. This method can be used for imaging and microsurgery with a small probe for diagnosing, treating, and monitoring progression of diseased tissue in vivo, in real time, and with cellular precision.

Femtosecond laser microsurgery (FLMS) offers the higher precision for microsurgery inside three-dimensional (3D) tissue. Because of high peak intensities and short pulse durations, near infrared (NIR) femtosecond laser pulses are absorbed through nonlinear processes inside biological materials that are otherwise transparent to NIR wavelengths. The nonlinear absorption process occurs in the focal volume where the photon flux is sufficiently high and thus confines the ablation to a small volume in the focal plane. The highly localized and efficient absorption of femtosecond laser pulses requires very little energy for ablation. This microsurgery method thus provides the ability to operate with micron-scale precision and reduces collateral damage to surrounding non-target tissues.

The in vivo application of this surgical technique can be guided and monitored by an equally precise and penetrating 3D imaging technique, such as two-photon microscopy (TPM). In TPM, simultaneous absorption of two photons of NIR wavelengths excites fluorophores that usually absorb in the ultraviolet or visible wavelength ranges. Two-photon excitation provides intrinsic optical sectioning and large penetration depths down to 1.0 mm. By combining FLMS with TPM, surgical light can be guided with microscopic imaging capabilities deep inside a scattering tissue. The system 10 can therefore be used for treatment and diagnosis of various diseases as well as for in vivo monitoring of disease progression. The system 10, or portions thereof, such as the housing 11, for FLMS and TPM can be positioned in a small and flexible device.

Figure 2:
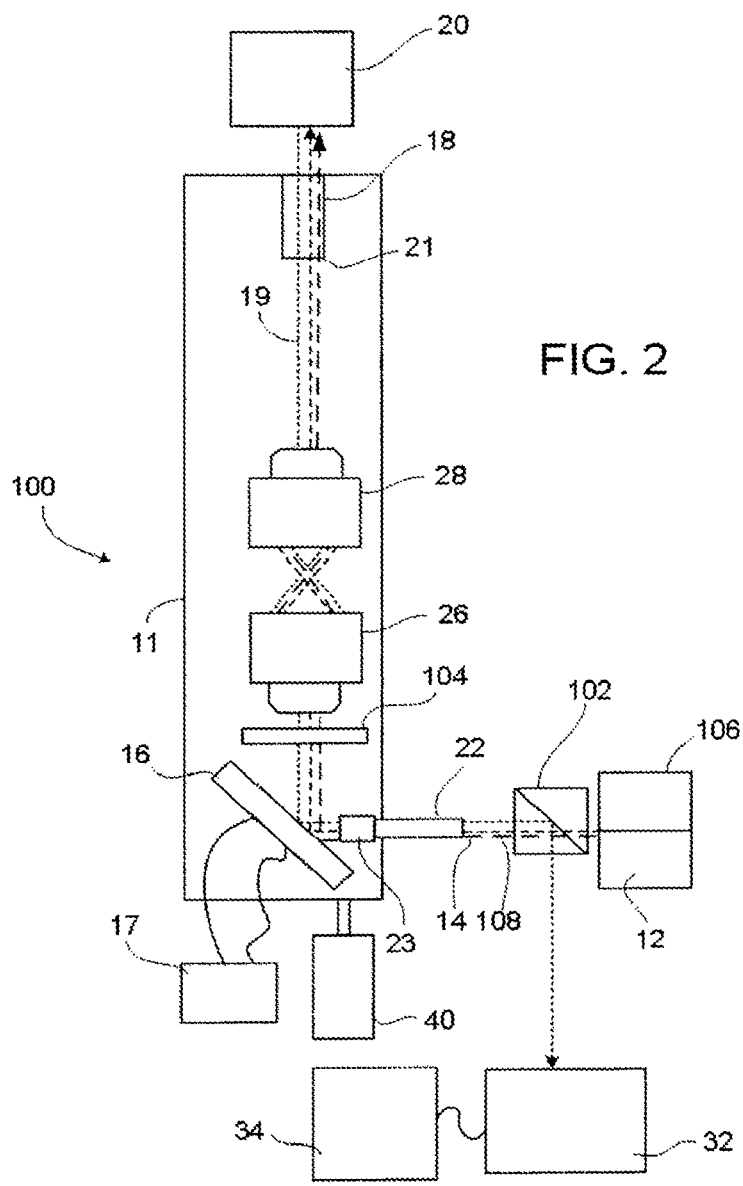
FIG. 2 is a schematic diagram illustrating an example confocal reflectance imaging and surgical system.

FIG. 2 is a schematic diagram illustrating an example system 100 for surgical manipulation of biological tissue in a subject and/or for confocal reflectance imaging in the subject. The system 100 comprises an ultra-fast pulsed laser surgical light source 12. The light source 12 is configured to produce laser light for surgical manipulation of biological tissue in the subject. For example, the light source 12 can be configured to produce one or more pulses of laser light having a duration of one nano-second or less. Optionally, the light source 12 is a picosecond or a femtosecond laser light source comprising a laser that can generate one or more laser pulses having a picosecond or femtosecond duration. The light source 12 can also be configured to produce laser pulses that are near-infrared.

The ultra-fast surgical laser light source 12 is located in communication with an optical delivery fiber 22. The optical delivery fiber 22 transmits light, surgical light 14, from the light source 12 into a housing 11. A polarizing beam splitter 102 can be located between the light source 10 and the delivery fiber 22. The polarizing beam splitter 102 allows passage of light from the light source 12 to the delivery fiber 22.

An objective lens 18 is also located in conjunction with the housing 11. The objective lens 18 is configured to receive light generated by the light source 12 that is transmitted into the housing 11 by the optical delivery fiber 22. Optionally, the optical delivery fiber 22 is an air-core photonic crystal fiber (PCF). Light transmitted along the fiber 22 can be directed through a collimating lens 23 and onto a scanning device 16. In other examples, instead of a scanning device 16, the optical delivery fiber 22 can be moved to provide scanning of light from the light source 12. For example, the fiber 22 can be moved using a piezoelectric scanning device that is configured to move the fiber to scan light from the light source 12.

The scanning device 16 can be a microelectromechanical (MEMS) scanner. If a MEMS scanner is used, it can be a two-axis gimbaled scanner with a reflective surface. The reflective surface can comprise a reflective coating that comprises metal. For example, the metal coating can comprise silver or aluminum. The scanning device 16 can be actuated to scan light from the optical delivery fiber 22 for transmission to the objective lens 18. For example, at least one processing unit 17 can be in communication with the scanning device 16. The processing unit 17 can be used to control the actuated movement of the scanning device for direction of light from the optical delivery fiber 22 to the objective lens 18. The scanning device 16 is also located in the housing 11 and the housing can be sized for endoscopic in vivo surgical procedures in the subject.

Light from the ultra-fast pulsed surgical laser light source 12, surgical light 14, directed onto the scanning device 16 can be further directed through a quarter wave plate 104 and through a pair of relay lenses 26 and 28 prior to contacting the back aperture 21 of the objective lens 18. Each relay lens of the pair 26 and 28 can be an aspherical lens. Optionally, the numerical aperture of each relay lens is 0.9 or less. At least a portion of the surgical light 14 from the light source 12 that contacts the back aperture 21 of the objective lens 18 is transmitted onto target tissue 20 of the subject. The objective lens 18 can focus surgical light 14 from the light source 12 into a focal volume where surgical manipulation can occur by the focused surgical light 14. The objective lens can have a numerical aperture of 0.4 or higher. As described above, the surgical light can cause photodamage or ablation of tissue in the subject. An actuator device 40, such as an electric motor, can be used to move the housing 11 towards or away from the target tissue 20.

The system 100 can further comprise a light source 106 for confocal reflectance imaging. The imaging light source 106 can be a pulsed or continuous wave light source used for confocal reflectance imaging. The light source 106 can also produce light that is infrared or near-infrared. For example, the light source 106 can optionally produce pulsed laser light that is infrared or near-infrared. Although the light source for surgery 12 and the light source for imaging 106 are separately depicted in this example, in other examples, the same light source can be used for both surgery and imaging. In these other examples, the light source can be adjustable such that it can produce light for surgical application and light for imaging application. Thus, a system comprising an ultra-fast pulsed surgical laser light source and further comprising an imaging light source can include only one actual light emitting component that can produce light configured for imaging and light configured for surgery.

The imaging light source 106 can therefore be configured to produce light for confocal reflectance imaging of biological tissue, referred to herein as imaging light 108. Similar to the surgical light 14, the imaging light 108 can be transmitted along the optical delivery fiber 22, through the collimating lens 23 and onto a scanning device 16. The imaging light 108 can be further directed through the pair of relay lenses 26 and 28 and through the objective lens 18. The objective lens is configured to transmit imaging light 108 to a region of interest of the target tissue 20.

The objective lens 18 is further configured to receive light from the target tissue 20. Light received from the target tissue can comprise light resulting from the backward scattering of light incident on the target tissue. For example, backward scattering of imaging light 108 can be received by the objective lens 18.

At least a portion of the light received by the objective lens 18 from the target tissue can be transmitted to a photodetector 32. The photodetector 32 is configured to detect at least a portion of the light transmitted to it. The photodetector can be in communication with at least one processing device 34 which can produce an image from light detected by the photodetector 32.

Portions of the system 100 can be located in the housing 11. Some portions of the system 100 can also be located outside of the housing 11. As described above, the housing 11 can be moved towards or away form the target tissue 20 using an actuating device. The system 100 can be used for surgical manipulation of biological tissue using light from the light source 12. Optionally, the system 100 can be used for confocal reflectance imaging in addition to its use for surgical manipulation of biological tissue. The system 100 can also be used for confocal reflectance imaging alone. Optionally, the system 100 can be used for surgical manipulation of biological tissue in addition to its use for confocal reflectance imaging.

Whether the system 100 is used for surgical manipulation of biological tissue alone, confocal reflectance imaging alone, or both surgical manipulation of biological tissue and confocal reflectance imaging, can be determined by an operator of the system. For example, if only surgical manipulation of biological tissue is desired, the system 100 can be used to transmit surgical light 14 to the target tissue. If only confocal reflectance imaging is desired, the system 100 can be used to transmit imaging light 108 to the target tissue. If both confocal reflectance imaging and surgical manipulation of biological tissue is desired, the system can be used to transmit imaging light 108 and surgical light 14 to the target tissue.

Figure 3:
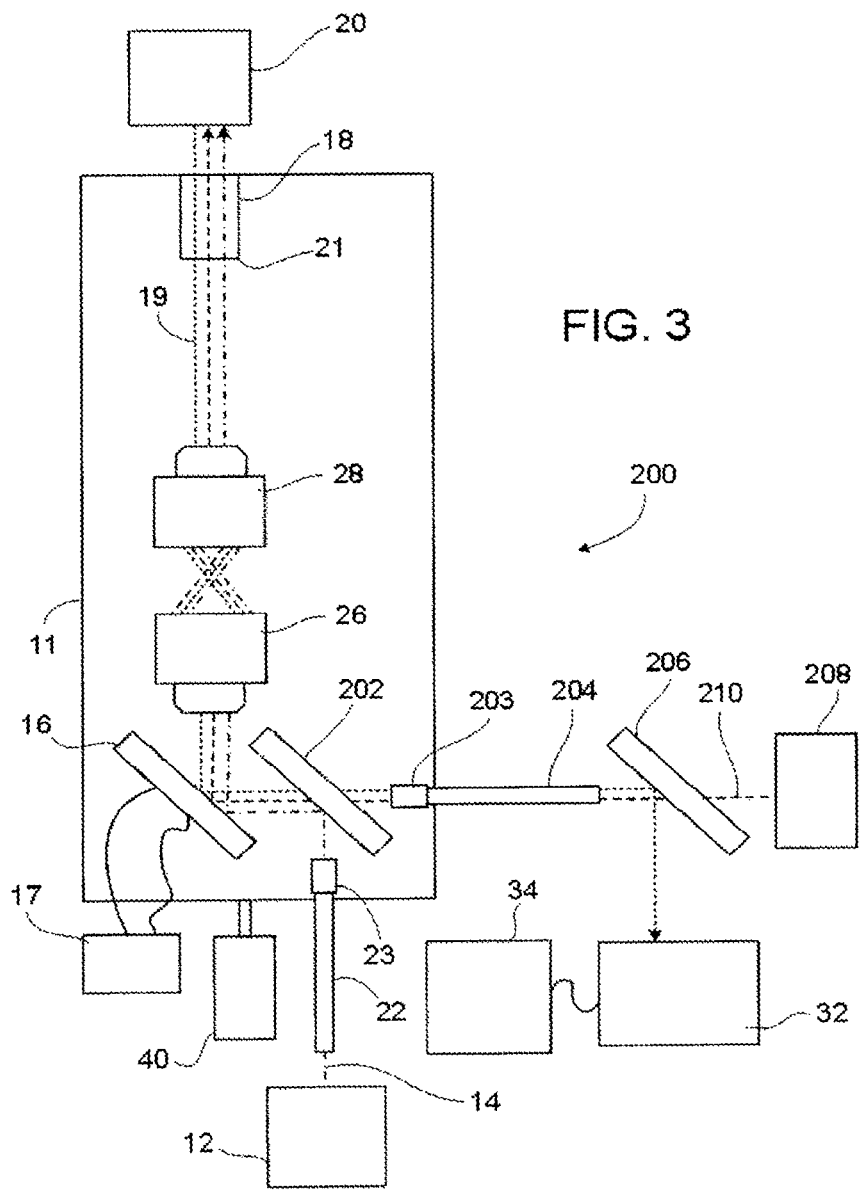
FIG. 3 is a schematic diagram illustrating an example confocal fluorescence imaging and surgical system.

FIG. 3 is a schematic diagram illustrating an example system 200 for surgical manipulation of biological tissue in a subject and/or for confocal fluorescence imaging in the subject. The system comprises an ultra-fast pulsed laser surgical light source 12. The light source 12 is configured to produce laser light for surgical manipulation of biological tissue in the subject. For example, the light source 12, can be configured to produce one or more pulses of laser light having a duration of one nano-second or less. Optionally, the light source 12 is a picosecond or a femtosecond laser light source comprising a laser that can generate one or more laser pulses having a picosecond or femtosecond duration. The light source 12 can also be configured to produce laser pulses that are near-infrared.

The ultra-fast surgical laser light source 12 is located in communication with an optical delivery fiber 22. The optical delivery fiber 22 transmits light, surgical light 14, from the light source 12 into a housing 11. An objective lens 18 is also located in conjunction with the housing 11. The objective lens 18 is configured to receive light generated by the light source 12 that is transmitted into the housing 11 by the optical delivery fiber 22. Optionally, the optical delivery fiber 22 is an air-core photonic crystal fiber (PCF). Light transmitted along the fiber 22 can be directed through a collimating lens 23 and onto a mirror 202 for direction onto a scanning device 16. In other examples, instead of a scanning device 16, the optical delivery fiber 22 can be moved to provide scanning of light from the light source 12. For example, the fiber 22 can be moved using a piezoelectric scanning device that is configured to move the fiber to scan light from the light source 12.

The scanning device 16 can be a microelectromechanical (MEMS) scanner. If a MEMS scanner is used, it can be a two-axis gimbaled scanner with a reflective surface. The reflective surface can comprise a reflective coating that comprises metal. For example, the metal coating can comprise silver or aluminum. The scanning device 16 can be actuated to scan light from the optical delivery fiber 22 for transmission to the objective lens 18. For example, at least one processing unit 17 can be in communication with the scanning device 16, which can be used to control the actuated movement of the scanning device 16 for direction of light from the optical delivery fiber 22 to the objective lens 18. The scanning device 16 is also located in the housing 11 and the housing can be sized for endoscopic in vivo surgical procedures in the subject.

Light from the ultra-fast pulsed surgical laser light source 12, surgical light 14, directed onto the scanning device 16 can be further directed through a pair of relay lenses 26 and 28 prior to contacting the back aperture 21 of the objective lens 18. Each relay lens of the pair 26 and 28 can be an aspherical lens. Optionally, the numerical aperture of each relay lens is 0.9 or less. At least a portion of the light from the light source 12 that contacts the back aperture 21 of the objective lens 18 is transmitted onto target tissue 20 of the subject. The objective lens 18 can focus light from the light source 12 into a focal volume where surgical manipulation can occur by the focused surgical light 14. The objective lens 18 can have a numerical aperture of 0.4 or higher. As described above, the surgical light can cause photodamage or ablation of tissue in the subject. An actuator device 40, such as an electric motor, can be used to move the housing 11 towards or away from the target tissue 20.

The system 200 can further comprise a light source 208 for confocal fluorescence imaging. The imaging light source 208 can be a continuous wave or pulsed light source used for confocal fluorescence imaging. Optionally, light source 208 can produce light that is visible, near-infrared, pulsed, or continuous wave. Although the light source for surgery 12 and the light source for imaging 208 are separately depicted in this example, in other examples the same light source can be used for both surgery and imaging. In these other examples, the light source can be adjustable such that it can produce light for surgical and light for imaging. Thus, a system 200 comprising an ultra-fast pulsed surgical laser light source and further comprising an imaging light source can include only one actual light emitting component that can produce light configured for imaging and light configured for surgery.

The imaging light source 208 can therefore be configured to produce light for confocal fluorescence imaging of biological tissue, referred to herein as imaging light 210. Similar to the surgical light 14, the imaging light 208 can be transmitted along the optical delivery fiber 204, through a collimating lens 203 and onto the scanning device 16. The imaging light 210 can also pass through a dichroic mirror 206 before being transmitted by the optical fiber 204. The imaging light 210 can be further directed through the pair of relay lenses 26 and 28 and through the objective lens 18. The objective lens is configured to transmit imaging light 210 to a region of interest of the target tissue 20.

The objective lens 18 is further configured to receive light from the target tissue. Light received from the target tissue can comprise light resulting from excitation of fluorophores in the target tissue. The excitation of the fluorophores can be caused by interaction of the imaging light 210 and the target tissue.

At least a portion of the light received by the objective lens 18 from the target tissue 20 can be transmitted to a photodetector 32. The photodetector 32 is configured to detect at least a portion of the light transmitted to it. The photodetector can be in communication with at least one processing device 34 which can produce an image from light detected by the photodetector 32.

Portions of the system 200 can be located in the housing 11. Some portions of the system 200 can also be located outside of the housing 11. As described above, the housing 11 can be moved towards or away form the target tissue 20 using an actuating device 40. The system 200 can be used for surgical manipulation of biological tissue using light from the light source 12. Optionally, the system 200 can be used for confocal fluorescence imaging in addition to its use for surgical manipulation of biological tissue. The system 200 can also be used for confocal fluorescence imaging alone. Optionally, the system 200 can be used for surgical manipulation of biological tissue in addition to is use for confocal fluorescence imaging.

Whether the system 200 is used for surgical manipulation of biological tissue alone, confocal fluorescence imaging alone, or both surgical manipulation of biological tissue and confocal fluorescence imaging can be determined by an operator of the system. For example, if only surgical manipulation of biological tissue is desired, the system 200 can be used to transmit surgical light 14 to the target tissue. If only confocal fluorescence imaging is desired, the system 200 can be used to transmit imaging light 210 to the target tissue. If both confocal fluorescence imaging and surgical manipulation of biological tissue is desired, the system can be used to transmit imaging light 210 and surgical light 14 to the target tissue.

Figure 4:
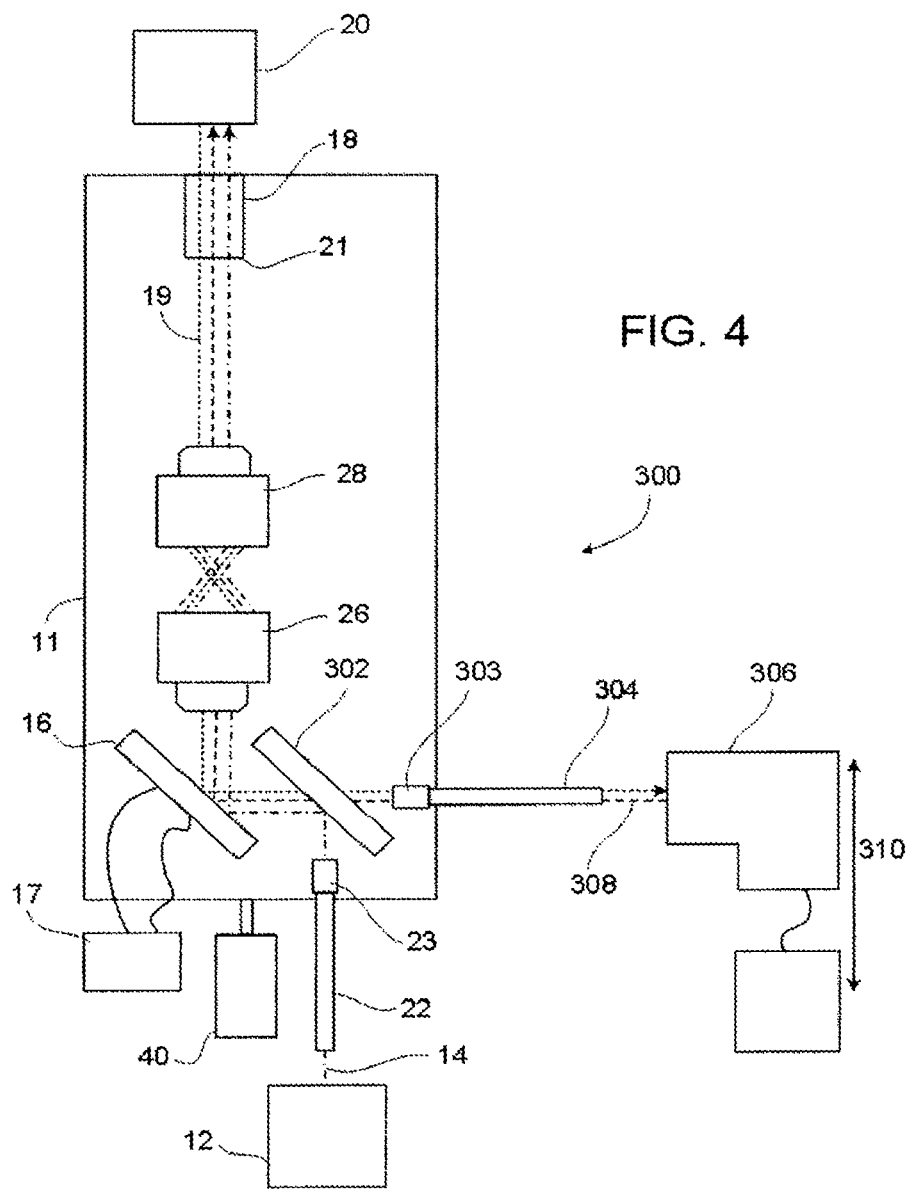
FIG. 4 is a schematic diagram illustrating an example optical coherence tomography (OCT) imaging and surgical system.

FIG. 4 is a schematic diagram illustrating an example system 300 for surgical manipulation of biological tissue in a subject and/or for optical coherence or optical coherence tomographic (OCT) imaging in the subject. The system comprises an ultra-fast pulsed laser surgical light source 12. The light source 12 is configured to produce laser light for surgical manipulation of biological tissue in the subject. For example, the light source 12, can be configured to produce one or more pulse of laser light having a duration of one nano-second or less. Optionally, the light source 12 is a picosecond or a femtosecond laser light source comprising a laser that can generate one or more laser pulses having a picosecond or femtosecond duration. The light source 12 can also be configured to produce laser pulses that are near-infrared.

The ultra-fast surgical laser light source 12 is located in communication with an optical delivery fiber 22. The optical delivery fiber 22 transmits light, surgical light 14, from the light source 12 into a housing 11. An objective lens 18 is also located in conjunction with the housing 11. The objective lens 18 is configured to receive light generated by the light source 12 that is transmitted into the housing 11 by the optical delivery fiber 22. Optionally, the optical delivery fiber 22 is an air-core photonic crystal fiber (PCF). Light transmitted along the fiber 22 can be directed through a collimating lens 23, onto a dichroic beamsplitter 302 that allows the OCT wavelengths to pass while transmitting the surgery light 14. The dichroic beamsplitter 302 can optionally be a hot or cold mirror for direction onto a scanning device 16. In other examples, instead of a scanning device 16, the optical delivery fiber 22 can be moved to provide scanning of light from the light source 12. For example, the fiber 22 can be moved using a piezoelectric scanning device that is configured to move the fiber to scan light from the light source 12.

The scanning device 16 can be a microelectromechanical (MEMS) scanner. If a MEMS scanner is used, it can be a two-axis gimbaled scanner with a reflective surface. The reflective surface can comprise a reflective coating that comprises metal. For example, the metal coating can comprise silver or aluminum. The scanning device 16 can be actuated to scan light from the optical delivery fiber 22 for transmission to the objective lens 18. For example, at least one processing unit 17 can be in communication with the scanning device 16 which can be used to control the actuated movement of the scanning device 16 for direction of light from the optical delivery fiber 22 to the objective lens 18. The scanning device 16 is also located in the housing 11 and the housing can be sized for endoscopic in vivo surgical procedures in the subject.

Light from the ultra-fast pulsed surgical laser light source 12, surgical light 14, directed onto the scanning device 16 can be further directed through a pair of relay lenses 26 and 28 prior to contacting the back aperture 21 of the objective lens 18. Each relay lens of the pair 26 and 28 can be an aspherical lens. Optionally, the numerical aperture of each relay lens is 0.9 or less. At least a portion of the light from the light source 12 that contacts the back aperture 21 of the objective lens 18 is transmitted onto target tissue 20 of the subject. The objective lens 18 can focus light from the light source 12 into a focal volume where surgical manipulation can occur by the focused surgical light 14. The objective lens can have a numerical aperture of 0.4 or higher. As described above, the surgical light can cause photodamage or ablation of tissue in the subject. An actuator device 40, such as an electric motor, can be used to move the housing 11 towards or away from the target tissue 20.

The system 300 can further comprise a light source 306 for OCT imaging. The imaging light source 306 can be a continuous wave or pulsed light source used for OCT imaging. Optionally, light source 306 can produce light that is broadband, visible, near-infrared, pulsed or continuous wave. Although the light source for surgery 12 and the light source for imaging 306 are separately depicted in this example, in other examples the same light source can be used for both surgery and imaging. In these other examples, the light source can be adjustable such that it can produce light for surgical application and light for imaging application. Thus, a system comprising an ultra-fast pulsed surgical laser light source and further comprising an imaging light source can include only one actual light emitting component that can produce light configured for imaging and light configured for surgery.

The imaging light source 306 can therefore be configured to produce light for OCT imaging of biological tissue, referred to herein as imaging light 308. Similar to the surgical light 14, the imaging light 308 can be transmitted along an optical delivery fiber 304, through a collimating lens 303 and onto the scanning device 16. The imaging light 308 can be further directed through the pair of relay lenses 26 and 28 and through the objective lens 18. The objective lens is configured to transmit imaging light 308 to a region of interest of the target tissue 20.

The objective lens 18 is further configured to receive light from the target tissue. Light received from the target tissue can comprise light resulting from the backward scattering of light incident on the target tissue. For example, backward scattering of imaging light 308 can be received by the objective lens 18.

At least a portion of the light received by the objective lens from the target tissue can be transmitted to an OCT imaging system 310. The OCT imaging system 310 is configured to produce an OCT image from light received 19 from the target tissue 20. An example OCT imaging system can optionally comprise a broadband light source, a delay line, an interferometer, and a photodetector. The OCT imaging system 310 can further comprise or be in communication with at least one processing device for producing an OCT image.

Portions of the system 300 can be located in the housing 11. Some portions of the system 300 can also be located outside of the housing 11. As described above, the housing 11 can be moved towards or away form the target tissue 20 using an actuating device 40. The system 300 can be used for surgical manipulation of biological tissue using light from the light source 12. Optionally, the system 300 can be used for OCT imaging in addition to its use for surgical manipulation of biological tissue. The system 300 can also be used for OCT imaging. Optionally, the system 300 can be used for surgical manipulation of biological tissue in addition to its use for OCT imaging.

Whether the system 300 is used for surgical manipulation of biological tissue alone, OCT imaging alone, or both surgical manipulation of biological tissue and OCT imaging can be determined by an operator of the system. For example, if only surgical manipulation of biological tissue is desired, the system 300 can be used to transmit surgical light 14 to the target tissue. If only OCT imaging is desired, the system 300 can be used to transmit imaging light 308 to the target tissue. If both OCT imaging and surgical manipulation of biological tissue is desired, the system can be used to transmit imaging light 308 and surgical light 14 to the target tissue.

The disclosed methods, systems, and devices can be used to image biological tissues in real-time, detect abnormalities, and treat the affected cells/tissues as necessary without the time or expense of conventional biopsy and with greater resolution than conventional diagnostics (MRI, PET, CT, ultrasound, white-light endoscopy).

Applications include medical endoscopy (for example, multiphoton fluorescence imaging of epithelial tissues for detection of neoplasia), dermal pathologies, pathologies of the larynx, oral cavity, and esophagus (including but not limited to, cancer), in vivo biological research, and the like.

Figure 5:
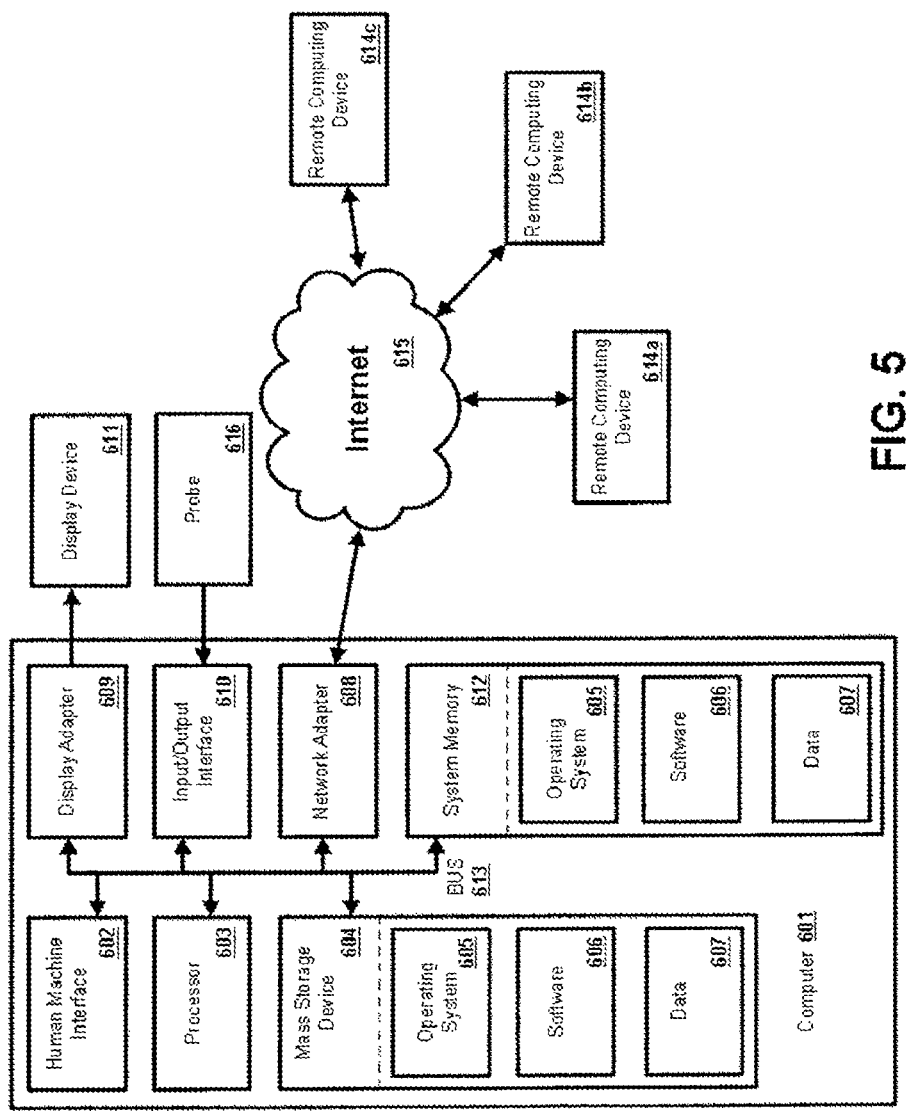
FIG. 5 is schematic diagram illustrating an exemplary operating environment for use with the disclosed systems, devices and methods.

The described systems can comprise one or more processing devices (e.g. 34 and 17). FIG. 5 is a block diagram illustrating an exemplary operating environment for performing operations of the described systems, devices and methods. One skilled in the art will appreciate that this is a functional description and that the respective functions can be performed by software, hardware, or a combination of software and hardware. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods, devices and systems can be operational with numerous other general purpose or special purpose computing system environments or configurations. Examples of well known computing systems, environments, and/or configurations that can be suitable for use with the system and method comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods, devices and systems can be performed by software components. The disclosed systems, devices, and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems, devices, and methods disclosed herein can be implemented via a general-purpose computing device in the form of a computer 601. The components of the computer 601 can comprise, but are not limited to, one or more processors or processing units 603, a system memory 612, and a system bus 613 that couples various system components including the processor 603 to the system memory 612. In the case of multiple processing units 603, the system can utilize parallel computing.

The system bus 613 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus also known as a Mezzanine bus. The bus 613, and all buses specified in this description can also be implemented over a wired or wireless network connection and each of the subsystems, including the processor 603, a mass storage device 604, an operating system 605, software 606, data 607, a network adapter 608, system memory 612, an Input/Output Interface 610, a display adapter 609, a display device 611, and a human machine interface 602, can be contained within one or more remote computing devices 614a,b,c at physically separate locations, connected through buses of this form, in effect implementing a fully distributed system.

The computer 601 typically comprises a variety of computer readable media. Exemplary readable media can be any available media that is accessible by the computer 601 and comprises, for example and not meant to be limiting, both volatile and non-volatile media, removable and non-removable media. The system memory 612 comprises computer readable media in the form of volatile memory, such as random access memory (RAM), and/or non-volatile memory, such as read only memory (ROM). The system memory 612 typically contains data such as data 607 and/or program modules such as operating system 605 and software 606 that are immediately accessible to and/or are presently operated on by the processing unit 603.

Figure 6:
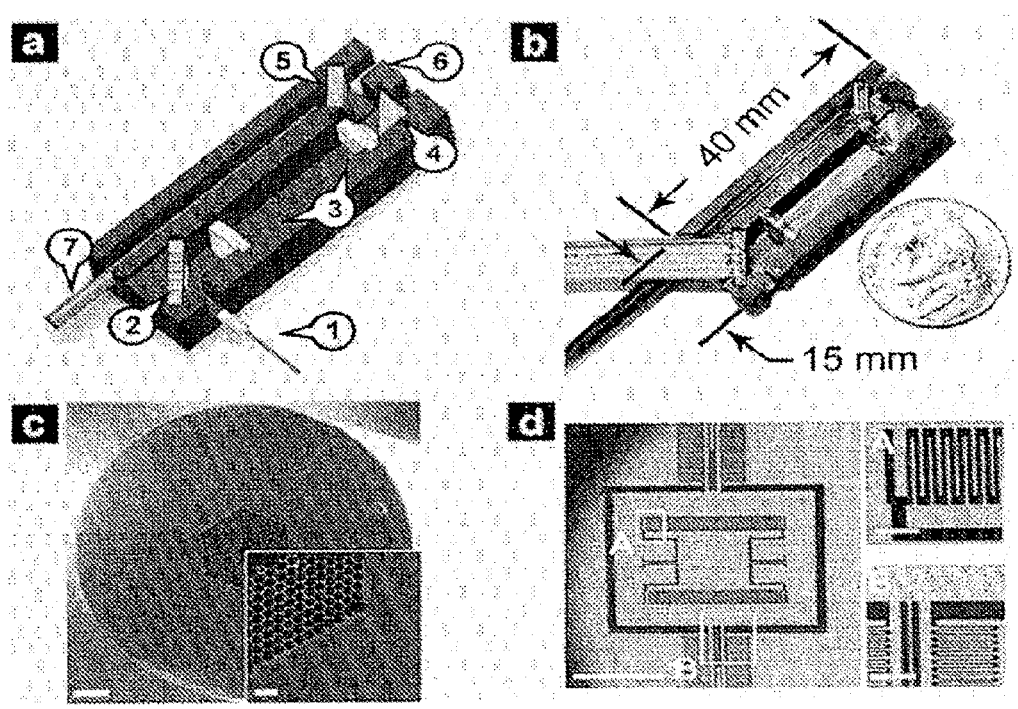
FIG. 6a is a perspective illustration of an exemplary two-photon microscopy and femtolaser microsurgery (TPM/FLMS) probe.
FIG. 6b is a photograph of an exemplary TPM/FLMS probe, including relevant dimensions, but not displaying fiber for laser delivery or lid for sealing out stray light.
FIG. 6c is a scanning electron microscope (SEM) micrograph of an exemplary photonic crystal fiber used for delivery of ultrashort laser pulses in the system; scale bar is 15 μm (3 μm inset).
FIG. 6d is a scanning electron microscope (SEM) micrograph of an exemplary micro-scanning device used for scanning and positioning of ultrashort laser pulses in the system; scale bar is 600 μm (120 μm inset).

In another aspect, the computer 601 can also comprise other removable/non-removable, volatile/non-volatile computer storage media. By way of example, FIG. 6 illustrates a mass storage device 604 which can provide non-volatile storage of computer code, computer readable instructions, data structures, program modules, and other data for the computer 601. For example and not meant to be limiting, a mass storage device 604 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 604, including by way of example, an operating system 605 and software 606. Each of the operating system 605 and software 606 (or some combination thereof) can comprise elements of the programming and the software 606. Data 607 can also be stored on the mass storage device 604. Data 607 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 601 via an input device. Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 603 via a human machine interface 602 that is coupled to the system bus 613, but can be connected by other interface and bus structures, such as a parallel port, game port, an IEEE 1394 Port (also known as a Firewire port), a serial port, or a universal serial bus (USB).

In yet another aspect, a display device 611 can also be connected to the system bus 613 via an interface, such as a display adapter 609. It is contemplated that the computer 601 can have more than one display adapter 609 and the computer 601 can have more than one display device 611. For example, a display device can be a monitor, an LCD (Liquid Crystal Display), or a projector. In addition to the display device 611, other output peripheral devices can comprise components such as speakers and a printer which can be connected to the computer 601 via Input/Output Interface 610. In one aspect, a probe 616, can be coupled to the computer 601 via Input/Output Interface 610.

The computer 601 can operate in a networked environment using logical connections to one or more remote computing devices 614a,b,c. By way of example, a remote computing device can be a personal computer, portable computer, a server, a router, a network computer, a peer device or other common network node, and so on. Logical connections between the computer 601 and a remote computing device 614a,b,c can be made via a local area network (LAN) and a general wide area network (WAN). Such network connections can be through a network adapter 608. A network adapter 608 can be implemented in both wired and wireless environments. Such networking environments are conventional and commonplace in offices, enterprise-wide computer networks, intranets, and the Internet 615.

For purposes of illustration, application programs and other executable program components such as the operating system 605 are illustrated herein as discrete blocks, although it is recognized that such programs and components reside at various times in different storage components of the computing device 601, and are executed by the data processor(s) of the computer. An implementation of software 606 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise computer storage media and communications media. Computer storage media comprise volatile and non-volatile, removable and non-removable media implemented in any method or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods, devices and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

EXAMPLES

Two-photon Microscopy (TPM) Femtolaser Microsurgery (FLMS) System

FIG. 6, is an illustration of portions of an exemplary TPM/FLMS system. The TPM/FLMS system can comprise a 10×15×40 mm³ miniaturized two-photon microscope and femtosecond laser microsurgery probe. As shown in FIG. 6a, the probe can comprise 1) air-core PCF and GRIN collimating lens, 2) two-axis MEMS scanning mirror, 3) miniature aspheric relay lenses, 4) mirror, 5) hot mirror, 6) 0.46-NA GRIN objective lens, and 7) 2 mm-core plastic optical fiber. The photograph in FIG. 6b shows the probe without the delivery fiber and the lid used to seal the probe. The PCF delivery fiber and its collimating GRIN lens are mounted separately and aligned to the probe during experiments. FIG. 6c illustrates scanning electron microscope (SEM) micrographs of the PCF core and cladding structure, and MEMS scanning mirror design. As shown in FIG. 6d the scale bars are 15 µm in FIG. 6c (3 µm in inset), and 600 µm in FIG. 6d (120 µm in inset).

The design can utilize an air-core photonic crystal fiber (PCF) (FIG. 6c), two-axis microelectromechanical systems (MEMS) scanning mirror (FIG. 6d), miniature relay lens system, and gradient index (GRIN) objective lens. (1) the air-core fiber allows delivery of high peak intensity femtosecond pulses for microsurgery, (2) the relay lenses image the scanning mirror to the back aperture of the objective lens, thus providing a large FOV with uniform excitation, (3) the relay lenses also expand the beam, thus allowing the use of a small and fast MEMS scanning mirror for high frame rates, while still overfilling the objective lens aperture for improved resolution, (4) both axes of the MEMS scanner are driven at resonance, allowing the use of low driving voltages to scan large FOV, and (5) the collection pathway is separated from the excitation fiber and uses a large numerical aperture (NA) fiber, providing improved collection efficiency.

The TPM/FLMS probe can use a one meter long air-core PCF (Air-6-800, Crystal Fiber A/S) to deliver femtosecond (fs) pulses for both imaging and microsurgery into a 10×15×40 mm³ Delrin housing (see FIG. 6c). Various lengths of fiber are contemplated, and can vary depending on the application. The fiber can have a peak transmission band from 750 nm to 800 nm and largely depolarize the laser pulses. Pulses for imaging (at 80 MHz repetition rate from Mai Tai®, Spectra Physics, Mountain View, Calif.) can be delivered at the minimum-dispersion wavelength of the PCF near 753 nm. The pulse duration was measured to be 152 fs after the fiber for 117 fs input pulse duration using an interferometric autocorrelator. Pulses for microsurgery (at 1 kHz repetition rate from Spitfire®, Spectra Physics, Mountain View, Calif.) were delivered near 780 nm, the operation wavelength of the chirped pulse amplifier. These pulses were prechirped by adjusting the compressor in the amplifier to compensate for the fiber dispersion, resulting in a pulse duration of 178 fs exiting the fiber. The beam coming out of the fiber was collimated to a $1/e^2$ diameter of 366 µm by a gradient index (GRIN) lens (0.46 NA, 1.8 mm diameter). The fiber tip and its collimating lens were held in a micropositioning stage which was aligned to send the collimated laser beam into the probe housing.

Inside the housing, the laser beam can be scanned using a two-axis gimbaled MEMS scanning mirror. The MEMS scanning mirror can be, for example, a bare silicon mirror, an aluminum-coated mirror, and the like. The mirror can be etched directly onto silicon-on-insulator and can be rotated about two axes using vertical electrostatic combs (see FIG. 6d). The 500×500 µm² mirror exhibits resonance frequencies of 1.54 kHz and 2.73 kHz.

Maximum optical beam deflections of ±10.5° for the outer axis and ±10° for the inner axis can be achieved by driving the mirrors with sinusoidal voltage signals at their resonant frequencies using peak voltage values of 80 volts. Above this voltage, no increase in deflection were observed. The corresponding number of resolvable spots was about 172×232. The collimated beam on the scanning mirror can be imaged onto the back aperture of a GRIN lens (0.46 NA, 210 µm working distance, and 1.8 mm diameter) through an aspherical lens pair which also serves as a 3.4× beam expander.

In one aspect, fluorescence emission can be collected by a 2-mm core plastic optical fiber (0.51 NA). The collection fiber can be positioned directly behind a 5×5 mm² hot mirror with a cut-off wavelength of 715 nm. The collected fluorescence can be delivered through one meter of the fiber and focused into a photomultiplier tube (H7422-40, Hamamatsu, Bridgewater, N.J.) by a 4 mm focal length lens with a Schott BG38 filter cutting scattered laser light.

For imaging, the laser beam can be Lissajous scanned by a software program driving both axes of the MEMS mirror at resonant frequencies with sinusoidal voltage signals. Using peak voltage values between 20-80 volts, the diameter of the FOV can be varied between 36-310 µm, respectively. The emission signal can be collected at 1 MHz rate (1 µs dwell time per pixel) and processed by the program to display a 256×256 pixel image at 10 Hz. The program can incorporate a variable pixel delay to compensate for phase delay between the driving voltage and the acquired signal, as well as phase delay between mirror axes. The pixel delay can be adjusted before imaging to reduce double and quadruple images arising from phase errors in the image reconstruction.

Sample Preparations

For experiments on a single layer of cells, MDMBA468 breast carcinoma cells were cultured in complete L15 medium on a tissue culture dish. Following replacement of the growth medium with a solution of 14 µM calcein AM in Dulbecco's Phosphate Buffered Saline (DPBS), the cells were incubated for 30 min at 37° C. Before imaging, the calcein solution was replaced with fresh DPBS.

For tissue phantoms, MDMBA468 breast carcinoma cells were suspended in a solution of 14 µM calcein AM in DBPS. The cell suspension was then spun down at 200 g for 7 min and resuspended in a buffered solution of high concentration type I collagen (BD Biosciences, San Jose, Calif.). The collagen/cell mixture was pipetted into a 500 µm deep silicon isolator (Molecular Probes®, Invitrogen, Carlsbad, Calif.) and then incubated for 25 minutes before imaging.

Image Processing

Post processing of images and vertical slice reconstructions were handled in ImageJ v1.37a, which is available from the National Institutes of Health, USA. Post-processing comprised averaging over 50 raw frames (5 seconds of imaging time); calibrating pixel dimensions and scaling for square pixels; and low-pass spatially filtering with a fast Fourier transform (FFT) algorithm at 1.2 cycles/µm cut-off frequency in the x and y directions. Filtering eliminated isolated pixels which were not sampled during the Lissajous scan and appear as sub-resolution zero-value pixels aligned in vertical and horizontal rows in the center of the image. The cut-off frequency was based on the measured resolution of the system, so as to not filter out any useful signal. Pixel dimensions were calibrated by moving the sample a known distance using piezoelectric stages and correlating this distance to pixels traversed in the image.

Imaging Characterization

The imaging characteristics (FOV, flatness, and resolution) of the probe were measured before testing the probe's potential for 3D imaging of live cells. To characterize the maximum extent and flatness of FOV, 1 µm fluorescent beads deposited onto a microscope slide were imaged. FIG. 7a displays a representative image demonstrating a maximum FOV of 310 µm in diameter. The limiting aperture for the maximum FOV was found to be the clear aperture of the second relay lens in the beam path. A fairly constant intensity over much of the field was observed. The extent of the FOV was varied between 36-310 µm by changing the peak voltage values from 20-80 volts, respectively.

Figure 7:
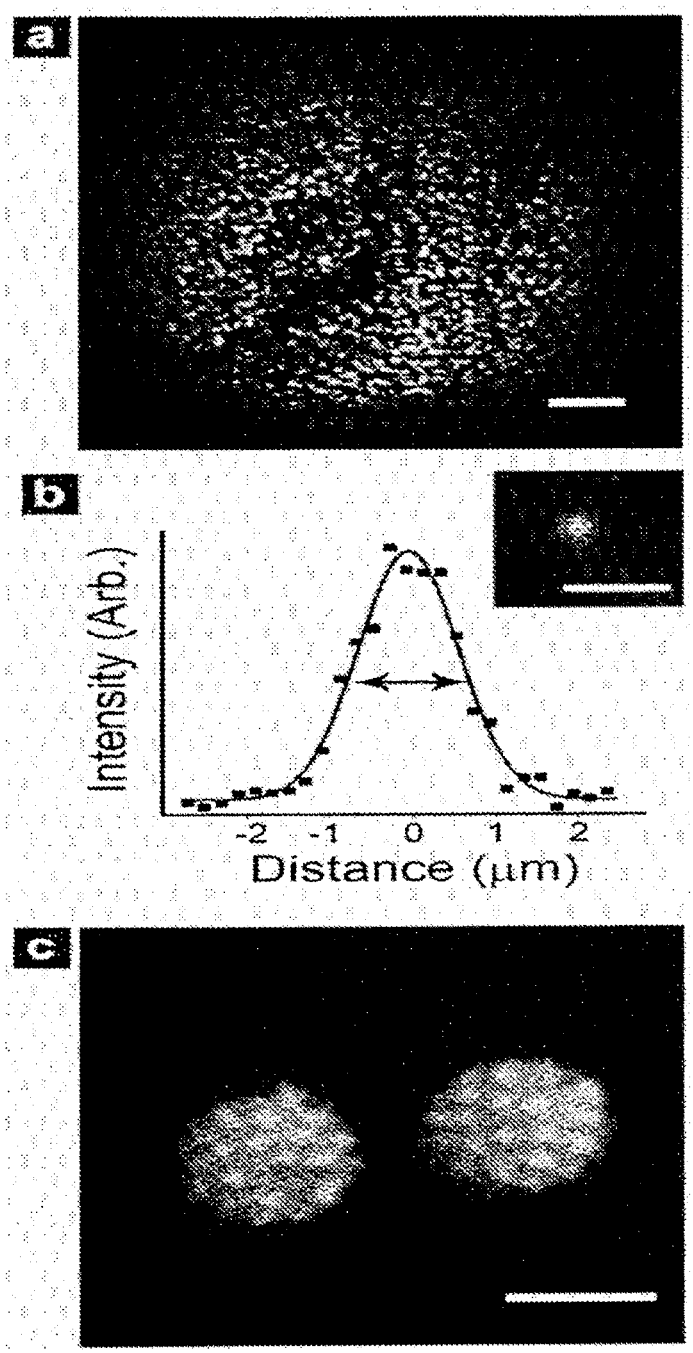
FIG. 7a is an exemplary multiphoton microscopy image of fluorescent beads taken using an example TPM/FMLS probe and demonstrating a field of view (FOV) of this device, namely 310 μm; scale bar is 50 μm.
FIG. 7b is a plot of the lateral fluorescence intensity profile measured during imaging of 100 nm fluorescent beads taken using an example TPM/FMLS probe. Measured values and the Gaussian curve fit is provided, with a full-width at half-maximum of 1.64 µm; inset shows original bead multiphoton image with scale bar of 5 µm.
FIG. 7c is an exemplary multiphoton microscopy image of fluorescent pollen grains taken using an example TPM/FMLS probe; scale bar is 20 µm.

FIG. 7 illustrates two-photon fluorescence imaging characterization of the TPM/FLMS probe. FIG. 7a illustrates 1 µm fluorescent beads on glass, demonstrating 310 µm maximum FOV. Laser power at the sample was measured to be 8.2 mW. FIG. 7a is a six frame average. FIG. 7b illustrates a representative lateral point spread function from 100 nm fluorescent beads in agar (shown in inset). Dots represent measured intensity values while the line is the Gaussian curve fit. FIG. 7c illustrates pollen grains. FIG. 7b and FIG. 7c are averaged over 5 seconds. FIG. 7a and FIG. 7c were spatially filtered with a low-pass FFT filter. Scale bars are 50 µm in FIG. 7a, 5 µm in FIG. 7b, and 50 µm in FIG. 7c.

Lateral and axial resolutions were determined experimentally by imaging 100 nm fluorescent beads in an agar gel across a 100 µm FOV to obtain the 3D point-spread function (PSF) of the probe. Using the Rayleigh criterion, the resolution was defined as the full width at half maximum of the Gaussian fit to the lateral and axial intensity profiles of an imaged bead, shown in FIG. 7b. The measured lateral and axial resolutions of the probe were 1.64±0.09 µm and 16.4±1.0 µm, respectively. The measurements were taken across 10 beads. Reported errors correspond to the standard error of the mean. The extended axial resolution had been previously attributed to spherical aberration from the GRIN lens. The resolution was not observed to vary significantly throughout the FOV, indicating that the beam was well imaged to the back aperture of the objective lens for all scanning angles.

The two-photon imaging capabilities of the probe were demonstrated using pollen grains deposited on a glass slide (30-4264, Carolina Biological Supply Co., Burlington, N.C.). FIG. 7c presents an image of two pollen grains, obtained using 9.0 mW average laser power at the sample. This image indicates the existence of pollen spines and demonstrates the resolving power of probe at the micrometer scale.

Cellular Imaging

To demonstrate 3D imaging of live cells in a turbid media, a collagen-based tissue phantom with breast carcinoma cells (MDMBA468) was prepared. Phantoms are engineered 3D tissue cultures that mimic optical properties of a real epithelial tissue, and are therefore useful in simulating tissue imaging capabilities. Before suspension in a tissue phantom, the cells were stained with 14 µM calcein acetoxymethyl (calcein AM). Calcein AM is a cell permeable dye that indicates cell vitality when it is converted into fluorescent calcein by esterases found in living cells. Images obtained immediately after uptake and activation of the calcein, showed a uniform fluorescence in living cells.

Figure 8:
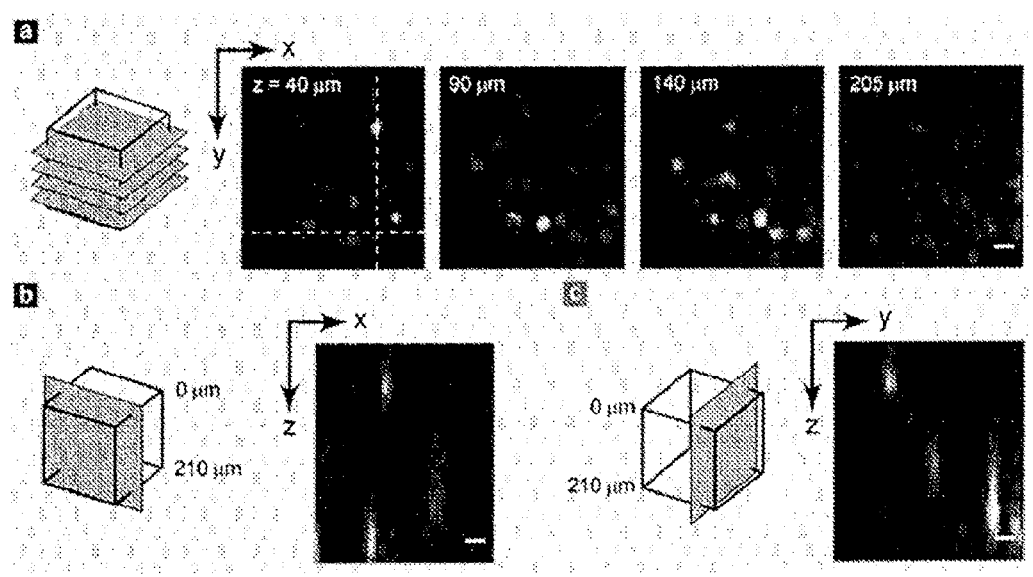
FIG. 8a is an exemplary series of x-y plane images of fluorescently labeled cancer cells in a 3D tissue-like media taken using an example TPM/FMLS probe, with images taken at different depths inside the 3D cell volume; scale bar is 20 µm.
FIG. 8b is an exemplary image of the x-z plane of the sample used in FIG. 8a, reconstructed from images such as those shown in FIG. 8a; scale bar is 20 µm.
FIG. 8c is an exemplary image of the y-z plane of the sample used in FIG. 8a, reconstructed from images such as those shown in FIG. 8a; scale bar is 20 µm.

FIG. 8a shows two-dimensional (2D) images of a 182×195 µm$^2$ lateral FOV taken at various depths below the surface of the tissue phantom. The probe was able to image down to 210 µm deep utilizing the full working distance of the GRIN objective lens. Average power at the sample was measured to be 17 mW. Despite the existence of scattering and absorption in the phantom the whole volume was imaged using the same laser excitation power. FIG. 8b and FIG. 8c show vertical slices through the imaged volume. The axial spacing between z steps is approximately 6.6 µm and was achieved by translating the sample in the z-direction using a piezoelectric stage. The images in FIG. 8 show the structure and orientation of cells at various depths embedded in a highly scattering media, though the 16.4 µm axial resolution results in elongation of the cells in the axial direction.

FIG. 8 illustrates three-dimensional imaging of live cancer cells in a tissue phantom. FIG. 8a TPM images of a 182×195 µm$^2$ FOV, taken at various depths beneath the surface. FIG. 8b and FIG. 8c show images of vertical slices reconstructed from lateral images taken 6.6 µm apart. Total imaging depth was 210 µm. Scale bars are 20 µm.

Cellular Microsurgery

To study the microsurgery capabilities of the probe, single cells were ablated both in a single cell layer and in a 3D tissue phantom. During these experiments, the cells were imaged before and immediately following ablation. For microsurgery, a flip mirror was used to direct the microsurgery laser into the fiber while the imaging laser was blocked. The MEMS mirror was static and undeflected during microsurgery, thus targeting the center of the FOV.

FIG. 9a and FIG. 9b present two-photon images of a single layer of live cancer cells before and after femtosecond laser microsurgery using a single pulse at 280 nJ pulse energy. Based on the PSF measurement and using the 1/e$^2$ diameter (~2.8 µm), this pulse energy corresponds to a peak laser intensity of 14 TW/cm$^2$. Ablation of the targeted cell was evidenced by the loss of its fluorescence signal, where the abrupt signal loss suggests that the membrane of the targeted cell was ruptured, releasing all of the calcein dye. As only a single laser pulse was used in this experiment, it was expected that the loss in fluorescence was due to ablation rather than photobleaching of the total volume of calcein, which would require longer exposures. Note that the high precision of fs-laser ablation allowed disintegration of the target cell while adjacent cells remain unharmed.

Figure 9:
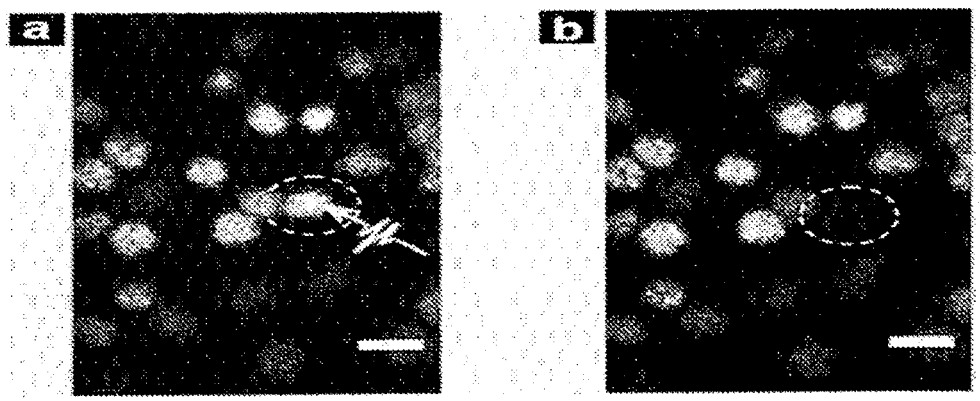
FIG. 9a is an exemplary image of a single layer of labeled cancer cells taken using an example TPM/FMLS probe before irradiation of the indicated cell by a single ultrashort laser pulse of 280 nJ pulse energy (~14 TW/cm$^2$ peak intensity); scale bar is 20 µm.
FIG. 9b is an exemplary image of a single layer of labeled cancer cells taken using an example TPM/FMLS probe after irradiation of the indicated cell by a single ultrashort laser pulse of 280 nJ pulse energy (~14 TW/cm$^2$ peak intensity); scale bar is 20 µm.

FIG. 9 illustrates combined two-photon microscopy and femtosecond laser microsurgery of a single layer of breast carcinoma cells. FIG. 9a shows a two photon image of a single layer of live breast carcinoma cells after uptake of calcein AM taken prior to irradiation with high intensity pulses. FIG. 9b shows the same FOV as FIG. 9a, immediately after irradiation with a single pulse at 280 nJ pulse energy. Note that the targeted cell has lost fluorescence while the neighboring cell is left intact.

Figure 10:
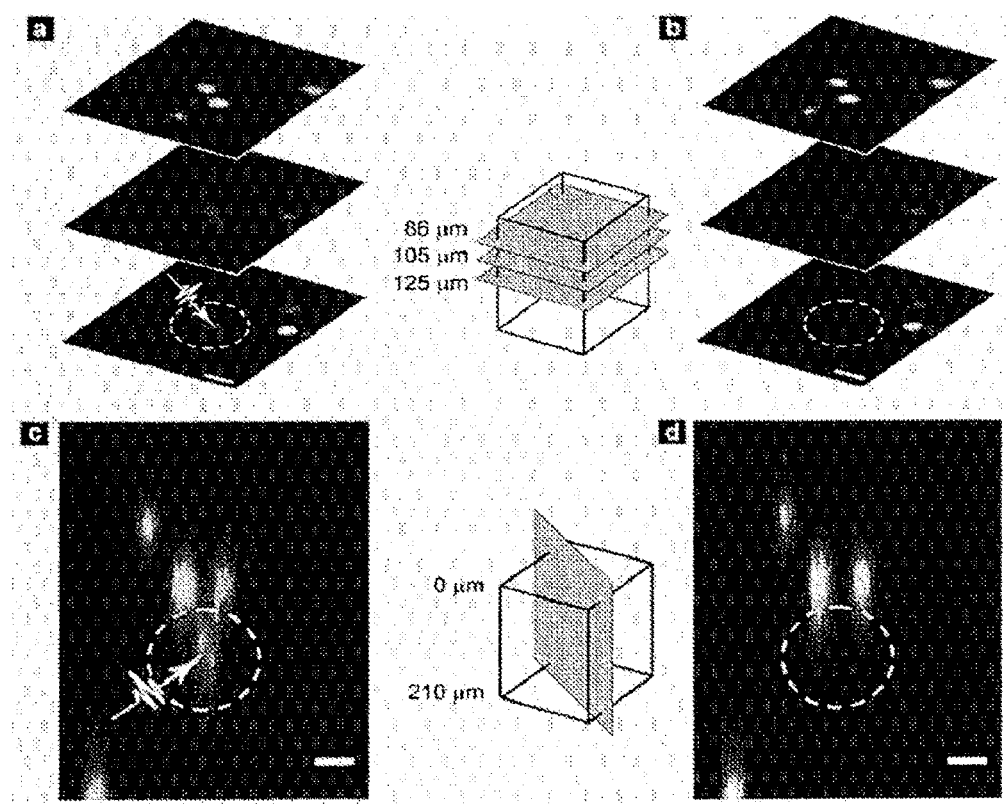
FIG. 10a is an exemplary series of x-y plane images taken using an example TPM/FMLS probe of fluorescently labeled cancer cells in a 3D tissue-like media, with images taken at different depths inside the 3D cell volume, before irradiation of the indicated cell by 5000 ultrashort laser pulses of 213 nJ pulse energy; scale bar is 20 µm.
FIG. 10b is an exemplary series of x-y plane images taken using an example TPM/FMLS probe of fluorescently labeled cancer cells in a 3D tissue-like media, with images taken at different depths inside the 3D cell volume, after irradiation of the indicated cell by 5000 ultrashort laser pulses of 213 nJ pulse energy; scale bar is 20 µm.
FIG. 10c is an exemplary image of the sample used in FIG. 10a, reconstructed from images such as those shown in FIG. 10a to give a vertical representation of the sample; scale bar is 20 µm.
FIG. 10d is an exemplary image of the sample used in FIG. 10b, reconstructed from images such as those shown in FIG. 10b to give a vertical representation of the sample; scale bar is 20 µm.

Ablation of cells was next investigated within a breast carcinoma tissue phantom. FIG. 10 presents images where a cell approximately 125 µm deep was targeted for ablation and destroyed. Here, 5000 pulses at 213 nJ per pulse were used. In this case, the immediate loss of cellular fluorescence was observed after irradiation with the microsurgery laser while the cells closest to the target remain intact. In addition to demonstrating microsurgery of cancer cells in turbid media, these images also demonstrate the utility of the probe for all-optical detection and ablation. Femtosecond laser ablation of subsurface cells in tissue provides physicians a noninvasive means of removing cells in sensitive areas, such as neural tissue.

FIG. 10 illustrates combined two-photon microscopy and femtosecond laser microsurgery of breast carcinoma cells in a collagen tissue phantom. FIG. 10a shows lateral slices with FOV of 116×160 µm² depicting a cell targeted for ablation, and the cells above it. FIG. 10b shows the same cells shown in FIG. 10a after irradiation of the targeted cells with 5000 pulses at 213 nJ pulse energy. FIG. 10c and FIG. 10d illustrate a vertical slice through the same targeted cell and the cells above it before and after laser irradiation, respectively. Total imaging depth was 210 µm and the axial spacing between lateral slices was 6.6 µm. Scale bars are 20 µm.

Furthermore, the laser dosages used for two-photon imaging were estimated to be at a safe level for cell vitality, which is important for sensitive clinical applications. Cell viability depends on both the incident peak laser intensity and the number of pulses at this intensity that the cell receives. Thus for comparison, the number of overlapping consecutive pulses was estimated as well as the peak intensity. The number of overlapping pulses was defined as the laser repetition rate divided by the product of the spot size and the scanning speed. For the probe, the slow axis MEMS scanning frequency and the ~116 µm FOV were used to arrive at a conservative estimate of scanning speed. Looking at peak intensity, the maximum average power used during cell imaging (17 mW used for imaging in the tissue phantom) corresponded to a peak intensity at the sample of ~13 $GW/cm^2$, which was below the maximum peak intensities found to be safe for long term two-photon imaging. In addition, the fast scanning speed used in the probe resulted in far fewer consecutive pulses delivered per spot at this intensity, which further reduced the overall laser dosage to the sample when imaging with the probe.

MEMS mirrors with high reflectivity in the NIR and miniature objective lenses with minimal spherical aberrations and higher NAs can be used for autofluorescence imaging capabilities. For example, to image weak fluorophores such as those found naturally within living cells. This autofluorescence signal is useful in many potential clinical applications for providing additional diagnostic information.

Two-photon contrast agents, such as bright luminescent gold nanorods, can be used to reduce the required excitation power by orders of magnitude in addition to providing molecularly specific imaging. Provided is a TPM/FLMS probe that can perform microsurgery through precise femtosecond laser ablation and provide 3D visualization of the operation region through two-photon imaging. In some aspects, imaging can be accomplished by Lissajous scanning of a two-axis gimballed MEMS mirror, achieving a maximum FOV of 310 µm and lateral and axial resolutions of 1.64 µm and 16.4 µm, respectively. The probe can incorporate a means of axial scanning, such as translating individual components or the system by a micro-motor, piezoelectric, or MEMS device for fully automated three-dimensional imaging. In some aspects, femtosecond laser microsurgery can be accomplished by delivering precompensated laser pulses with energies up to 280 nJ through an air core PCF.

Any patents or publications mentioned in the specification are indicative of the level of those skilled in the art. These patents and publications are herein incorporated by reference in their entirety to the same extent as if each individual publication was specifically and individually indicated to be incorporated by reference.

What is claimed is:

1. A system for surgical manipulation of biological tissue in a subject, comprising:
    an ultra-fast pulsed surgical laser light source configured to produce laser light with pulse energies sufficient for ablation of biological tissue, wherein the pulse energies are 50 nanojoules (nJ) or higher and wherein the ultra-fast pulsed surgical laser light has a pulse duration of less than one nanosecond;
    an air core optical delivery fiber having a core size;
    a focusing lens coupling the laser light having pulse energies sufficient for ablation of biological tissue with pulse energies of 50 nJ or higher and a pulse duration of less than one nanosecond from the light source to the optical delivery fiber;
    wherein the coupled laser light is guided in a single mode in the optical delivery fiber;
    wherein a focused beam size of the laser light from the laser light source coupled to the optical delivery fiber is smaller than the core size; and
    an objective lens having a numerical aperture (NA) for focusing light to a given spot in the tissue, wherein the optical delivery fiber is configured to direct the coupled laser light from the surgical laser light source for transmission to the objective lens, and wherein the objective lens having the NA is configured to focus the coupled laser light to the given spot in the tissue, the energy per unit of area within the spot where the laser light is focused being sufficient for ablation of biological tissue at the focus spot.

2. The system of claim 1, further comprising a scanning device configured to direct the laser light from the optical delivery fiber for transmission to the objective lens.

3. The system of claim 2, wherein the scanning device is a microelectromechanical scanning device.

4. The system of claim 3, wherein the micro electromechanical scanning device is a two-axis gimbaled scanner.

5. The system of claim 3, wherein the micro electromechanical scanning device comprises a reflective scanning surface.

6. The system of claim 5, wherein the reflective scanning surface comprises a metal coating.

7. The system of claim 6, wherein the metal is aluminum.

8. The system of claim 2, wherein the scanning device is a piezoelectric scanning device configured to move the optical fiber.

9. The system of claim 2, further comprising a collimating lens positioned between the optical delivery fiber and the scanning device.

10. The system of claim 1, wherein the ultra-fast pulsed surgical laser light source is configured to produce near infrared laser pulses.

11. The system of claim 1, wherein the pulse energies sufficient to cause ablation are sufficient to cause photo damage or removal of biological tissue located in the region of interest and wherein one or more laser pulses are configured to cause photo damage or removal of biological tissue in a focal volume in the region of interest.

12. The system of claim 1, wherein the pulse energies sufficient to cause ablation are sufficient to cause photo-damage or photo-stimulation or photo-activation of biological tissue located in the region of interest and wherein one or more laser pulses are configured to photo-damage or photo-stimulate or photo-activate biological tissue in a focal volume in the region of interest.

13. The system of claim 1, further comprising a prechirping system positioned between the optical delivery fiber and the surgical laser light source.

14. The system of claim 1, further comprising:
an imaging light source configured to produce light for imaging of biological tissue; and
a relay lens system, wherein light from the imaging light source is configured to be directed through the relay lens system for transmission to the objective lens, and
wherein the objective lens is configured to transmit light from the imaging light source to a region of interest in the subject and to receive light from the region of interest in the subject for imaging of biological tissue.

15. The system of claim 14, further comprising a scanning device configured to direct light for imaging and for ablation of biological tissue from the imaging light source and the ultra-fast pulsed surgical light source for transmission to the objective lens.

16. The system of claim 15, further comprising a collimating lens positioned between the optical delivery fiber and the scanning device.

17. The system of claim 14, further comprising a photodetector configured to detect at least a portion of the light received from the region of interest.

18. The system of claim 17, further comprising at least one processing device configured to produce an image of at least a portion of the region of interest from the detected light.

19. The system of claim 14, wherein the imaging light source comprises an ultra-fast pulsed laser.

20. The system of claim 19, wherein the ultra-fast pulsed laser for imaging is configured to produce a laser pulse having a duration of less than one nanosecond.

21. The system of claim 19, wherein the ultra-fast pulsed laser for imaging comprises a picosecond or femtosecond laser.

22. The system of claim 19, wherein the ultra-fast pulsed laser for imaging is configured to produce near infrared laser pulses.

23. The system of claim 14, wherein the imaging light source is configured to produce broad-band light.

24. The system of claim 14, wherein the imaging light source is configured to produce visible to near-infrared light.

25. The system of claim 14, wherein light received from the region of interest results from excitation of fluorophores in the region of interest.

26. The system of claim 25, wherein the fluorophores are excited by the light from the imaging light source directed onto the region of interest by the objective lens.

27. The system of claim 14, wherein light received from the region of interest results from generation of a harmonic of the incident light in the region of interest.

28. The system of claim 27, wherein the harmonic light is generated by the light from the imaging light source directed onto the region of interest by the objective lens.

29. The system of claim 27, wherein the light received from the region of interest results from generation of a second harmonic of the incident light in the region of interest.

30. The system of claim 14, wherein light received from the region of interest results from excitation of luminescence from nanoparticles in the region of interest.

31. The system of claim 30, wherein the luminescence from the nanoparticles is generated by the light from the imaging light source directed onto the region of interest by the objective lens.

32. The system of claim 30, wherein the nanoparticles are gold nanoparticles.

33. The system of claim 14, wherein light received from the region of interest results from the backward scattering of light incident on the region of interest.

34. The system of claim 33, wherein the backward scattered light originates from light from the imaging light source directed onto the region of interest by the objective lens.

35. The system of claim 14, wherein the relay lens system comprises an aspherical relay lens.

36. The system of claim 35, wherein the numerical aperture of the aspherical relay lens is 0.9 or less.

37. The system of claim 14, further comprising a pre chirping system positioned between the optical delivery fiber and the imaging light source.

38. The system of claim 14, wherein the objective lens has a numerical aperture of 0.4 or higher.

39. A system for imaging and ablation of biological tissue in a subject, comprising:
an imaging light source configured to produce light for imaging of biological tissue;
an air core optical delivery fiber having a core size;
a relay lens system;
a focusing lens coupling the laser light from the light source to the optical delivery fiber;
an objective lens, wherein the optical delivery fiber is configured to direct light from the imaging light source through the relay lens system for transmission onto the objective lens, and wherein the objective lens is configured to direct light transmitted onto it from the imaging light source to a region of interest in the subject and to receive light from the region of interest;
a photodetector configured to detect at least a portion of the light received from the region of interest; and
an ultra-fast pulsed surgical laser light source configured to produce laser light with a pulse energy sufficient for ablation of biological tissue, wherein the pulse energies are 50 nanojoules (nJ) or higher and wherein the ultra-fast pulsed surgical laser light has a pulse duration of less than one nanosecond;
wherein the coupled laser light having the pulse energies of 50 nanojoules (nJ) or higher and a pulse duration of less than one nanosecond is guided in a single mode in the optical delivery fiber,
wherein a focus beam size of the laser light from the laser light source coupled to the optical delivery fiber is smaller than the core size of the fiber,
wherein produced laser light having the pulse energies of 50 nanojoules (nJ) or higher and a pulse duration of less than one nanosecond is configured to be directed from the ultra-fast pulsed surgical laser light source to the objective lens, and
wherein the objective lens is configured to transmit light having the pulse energies of 50 nanojoules (nJ) or higher and a pulse duration of less than one nanosecond from the ultra-fast surgical laser light source to a region of interest in the subject for ablation of biological tissue.

40. The system of claim 39, further comprising a scanning device configured to direct light for imaging from the optical delivery fiber for transmission to the objective lens.

41. The system of claim 40, wherein the scanning device is a microelectromechanical scanning device.

42. The system of claim 41, wherein the microelectromechanical scanning device is a two-axis gimbaled scanner.

43. The system of claim 41, wherein the microelectromechanical scanning device comprises a reflective scanning surface.

44. The system of claim 43, wherein the reflective scanning surface comprises a metal coating.

45. The system of claim 44, wherein the metal is aluminum.

46. The system of claim 40, wherein the scanning device is a piezoelectric scanning device configured to move the optical delivery fiber.

47. The system of claim 40, further comprising a collimating lens positioned between the optical delivery fiber and the scanning device.

48. The system of claim 39, further comprising at least one processing device configured to produce an image of at least a portion of the region of interest from the detected light.

49. The system of claim 39, wherein the imaging light source comprises an ultra-fast pulsed laser.

50. The system of claim 49, wherein the ultra-fast pulsed laser of the imaging light source is configured to produce a laser pulse having a duration of less than one nanosecond.

51. The system of claim 49, wherein the ultra-fast pulsed laser of the imaging light source comprises a picosecond or femtosecond laser.

52. The system of claim 49, wherein the ultra-fast pulsed laser of the imaging light source is configured to produce near infrared laser pulses.

53. The system of claim 39, wherein the imaging light source is configured to produce broad-band light.

54. The system of claim 39, wherein the imaging light source is configured to produce visible to near-infrared light.

55. The system of claim 39, wherein the relay lens system comprises an aspherical relay lens.

56. The system of claim 55, wherein the numerical aperture of the aspherical relay lens is 0.9 or less.

57. The system of claim 39, further comprising a prechirping system positioned between the optical delivery fiber and the imaging light source.

58. The system of claim 39, wherein the objective lens has a numerical aperture of 0.4 or higher.

59. The system of claim 39, further comprising a scanning device configured to direct light for imaging and ablation of biological tissue from the imaging light source and from the ultra-fast pulsed surgical laser light source for transmission to the objective lens.

60. The claim of claim 39, wherein the ultra-fast pulsed Surgical laser is configured to produce near infrared laser pulses.

61. A system for surgical ablation and imaging in a subject, comprising:
an imaging light source configured to produce laser light for imaging of biological tissue;
an ultra-fast pulsed surgical laser light source configured to produce laser light with pulse energies sufficient for ablation of biological tissue; wherein the pulse energies are 50 nanojoules (nJ) or higher and wherein the ultra-fast pulsed surgical laser light has a pulse duration of less than one nanosecond;
an air core optical delivery fiber having a core size, wherein a focused beam size of the light from the laser light source coupled to the optical delivery fiber is smaller than the core size of the fiber;
a focusing lens coupling the laser light having pulse energies sufficient for ablation of biological tissue with pulse energies of 50 nJ or higher and a pulse duration of less than one nanosecond from the light source to the optical delivery fiber, wherein the light is guided in single mode;
a microelectromechanical scanning device;
a relay lens system;
an objective lens, wherein the microelectromechanical scanning device is configured to direct light from the imaging and surgical laser light sources through the relay lens system for transmission onto the objective lens, and wherein the objective lens is configured to direct light transmitted onto it to a region of interest in the subject and to receive light from the region of interest;
an optical transmitter in communication with the objective lens, wherein the optical transmitter is adapted to transmit at least a portion of the light received from the region of interest by the objective lens; and
a photodetector in communication with the optical transmitter and configured to detect at least a portion of the light transmitted by the optical transmitter.

62. The system of claim 61, further comprising at least one processing device configured to produce an image of at least a portion of the region of interest from the detected light.

63. A device for surgical manipulation of biological tissue in a subject, comprising:
an air core optical delivery fiber having a core size;
a focusing lens coupling laser light having pulse energies of 50 nJ or higher and a pulse duration of less than one nanosecond from an ultra-fast pulsed surgical laser light source to the optical delivery fiber; and
an objective lens, wherein the optical delivery fiber is configured to direct light having pulse energies of 50 nJ or higher and a pulse duration of less than one nanosecond from the ultra-fast pulsed surgical laser light source for transmission to the objective lens,
wherein the laser light is guided in a single mode in the optical delivery fiber,
wherein a focused beam size of the laser light from the laser light source coupled to the optical delivery fiber is smaller than the core size of the fiber,
wherein the objective lens is configured to transmit light having pulse energies of 50 nJ or higher and a pulse duration of less than one nanosecond from the ultra-fast pulsed surgical laser light source directed to it to a region of interest in the subject for ablation of biological tissue in the subject.

64. The device of claim 63, further comprising:
a relay lens system, wherein light from an imaging light source is configured to be directed through the relay lens system for transmission to the objective lens, and
wherein the objective lens is configured to transmit light from the imaging light source directed to it to a region of interest in the subject and to receive light from the region of interest in the subject for imaging of biological tissue in the subject.

65. A device for imaging and surgical manipulation of biological tissue in a subject, comprising:
an air core optical delivery fiber having a core size;
a relay lens system;
a focusing lens coupling laser light from a light source to the optical delivery fiber; and
an objective lens, wherein the optical delivery fiber is configured to direct light from an imaging light source through the relay lens system for transmission onto the objective lens, wherein the objective lens is configured to direct light transmitted onto it from the imaging light source to a region of interest in the subject and to receive light from the region of interest for imaging biological tissue, wherein the optical delivery fiber is further configured to direct surgical laser light from an ultra-fast pulsed surgical laser the directed surgical laser light from the ultra-fast pulsed surgical laser having pulse energies of 50 nJ or higher and a pulse duration of less than one nanosecond light source to the objective lens, wherein the surgical laser light is guided in a single mode in the optical delivery fiber, wherein a focused beam size of the surgical laser light from the laser light source coupled to the optical delivery fiber is smaller than the core size of the fiber, wherein the objective lens is configured to transmit surgical laser light from the surgical laser light source to a region of interest in the subject for ablation of biological tissue in the subject.

* * * * *